(12) United States Patent
Mujwid et al.

(10) Patent No.: US 11,337,814 B2
(45) Date of Patent: May 24, 2022

(54) PUMP ASSEMBLY FOR A PENILE PROSTHESIS HAVING AN OUTER PROTECTIVE CASING

(71) Applicant: Boston Scientific Scimed, Inc., Maple Grove, MN (US)

(72) Inventors: James Ryan Mujwid, Hudson, WI (US); Ryan Earl Fredrick, Eden Prairie, MN (US); Mark Edward DiLoreto, Chaska, MN (US); John Anders Bostrom, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 261 days.

(21) Appl. No.: 16/680,129

(22) Filed: Nov. 11, 2019

(65) Prior Publication Data

US 2020/0155318 A1 May 21, 2020

Related U.S. Application Data

(60) Provisional application No. 62/768,402, filed on Nov. 16, 2018.

(51) Int. Cl.
*A61F 2/26* (2006.01)

(52) U.S. Cl.
CPC ........ *A61F 2/26* (2013.01); *A61F 2230/0069* (2013.01)

(58) Field of Classification Search
CPC ......................................................... A61F 2/26
See application file for complete search history.

(56) References Cited

U.S. PATENT DOCUMENTS

| | | | |
|---|---|---|---|
| 4,566,446 | A | 1/1986 | Fogarty et al. |
| 4,881,530 | A | 11/1989 | Trick et al. |
| 5,167,611 | A | 12/1992 | Cowan |
| 7,914,439 | B2 | 3/2011 | Kuyava et al. |
| 8,276,591 | B2 | 10/2012 | Henkel et al. |
| 8,939,889 | B1 | 1/2015 | Chechik |
| D725,271 | S | 3/2015 | Chechik |
| D725,777 | S | 3/2015 | Chechik |
| D739,530 | S | 9/2015 | Chechik |
| 2002/0082709 | A1 | 6/2002 | Almli et al. |
| 2004/0138523 | A1 | 7/2004 | Kuyava et al. |
| 2006/0135845 | A1 | 6/2006 | Kuyava et al. |
| 2007/0142700 | A1 | 6/2007 | Fogarty et al. |
| 2018/0318085 | A1 | 11/2018 | Felton et al. |

FOREIGN PATENT DOCUMENTS

WO  2020112443 A1  6/2020

OTHER PUBLICATIONS

International Search Report and Written Opinion for Application No. PCT/US2019/060938, dated Apr. 14, 2020, 11 pages.
International Search Report and Written Opinion for PCT Application No. PCT/US2020/031656, dated Jul. 30, 2020, 16 pages.

*Primary Examiner* — John P Lacyk
(74) *Attorney, Agent, or Firm* — Brake Hughes Bellermann LLP

(57) ABSTRACT

According to an aspect, an inflatable penile prosthesis includes a fluid reservoir configured to hold fluid, an inflatable member, and a pump assembly configured to transfer the fluid between the fluid reservoir and the inflatable member. The pump assembly includes a valve body having one or more valves, and an outer protective casing disposed over the valve body.

20 Claims, 28 Drawing Sheets

PUMP ASSEMBLY FOR A PENILE PROSTHESIS HAVING AN OUTER PROTECTIVE CASING

CROSS-REFERENCE TO RELATED APPLICATION

This application is a Nonprovisional of, and claims priority to, U.S. Patent Application No. 62/768,402, filed on Nov. 16, 2018, entitled "PUMP ASSEMBLY FOR A PENILE PROSTHESIS HAVING AN OUTER PROTECTIVE CASING", which is incorporated by reference herein in its entirety.

TECHNICAL FIELD

This disclosure relates generally to bodily implants and more specifically to bodily implants, such as penile prosthesis that includes an outer protective casing disposed over a valve block of a pump assembly.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. The pump mechanism may include a valve body that is used by patients as a place to hold the device while they are pumping the device to achieve inflation. However, according to some existing designs, patients have reported issues with locating the deflation mechanism and differentiating the valve body from the pump bulb.

SUMMARY

According to an aspect, an inflatable penile prosthesis includes a fluid reservoir configured to hold fluid, an inflatable member, and a pump assembly configured to transfer the fluid between the fluid reservoir and the inflatable member. The pump assembly includes a valve body having one or more valves, and an outer protective casing disposed over the valve body.

According to some aspects, the inflatable penile prosthesis may include one or more of the following features (or any combination thereof). The outer protective casing includes a tactile feature configured to assist a user to locate a deflation mode actuator of the inflatable penile prosthesis. The tactile feature includes a plurality of ridges. The tactile feature includes a depression. The outer protective casing includes an opening, and the deflation mode actuator extends through the opening of the outer protective casing. The pump assembly includes a pump bulb, a plurality of fluid ports, and a deflation mode actuator. The outer protective casing includes a first end portion defining a first opening, and a second end portion defining a second opening. The outer protective casing defines a third opening, the pump bulb extends through the first opening, the plurality of fluid ports extends through the second opening, and the deflation mode actuator extends through the third opening. The outer protective casing includes a protruded side portion having a three-dimensional shape, and the protruded side portion has a surface that defines at least one ridge. The outer protective casing includes a polymer material. The outer protective casing includes a silicone material.

According to an aspect, an inflatable penile prosthesis includes a fluid reservoir configured to hold fluid, an inflatable member, and a pump assembly configured to transfer the fluid between the fluid reservoir and the inflatable member. The pump assembly includes a deflation mode actuator, a valve body having one or more valves, and an outer protective casing disposed over the valve body, where the outer protective casing has a tactile feature configured to assist a user locate the deflation mode actuator.

According to some aspects, the inflatable penile prosthesis may include one or more of the above/below features (or any combination thereof). The tactile feature includes a plurality of ridges. The tactile feature includes a depression. The pump assembly includes a pump bulb, and a plurality of fluid ports, and the outer protective casing includes a first end portion defining a first opening, and a second end portion defining a second opening. The outer protective casing defines a third opening. The pump bulb extends through the first opening, the plurality of fluid ports extend through the second opening, and the deflation mode actuator extends through the third opening. The outer protective casing includes a first protruded side portion, and a second protruded side portion, where at least one of the first protruded side portion and the second protruded side portion defines at least one ridge. The outer protective casing includes a central portion, and a plurality of projections extending from the central portion, where projections define at least one groove. The outer protective casing includes a material that is different than the valve body.

According to an aspect, a pump assembly for an inflatable penile prosthesis includes a valve body having one or more valves, a deflation mode actuator movably coupled to the valve body, a pump bulb coupled to the valve body, one or more fluid ports coupled to the valve body, and an outer protective casing disposed over the valve body. The outer protective casing has a tactile feature configured to assist a user to locate the deflation mode actuator.

According to some aspects, the pump assembly may include any one or more of the above/below features (or any combination thereof). The outer protective casing includes a first end portion defining a first opening, a second end portion defining a second opening, and a side portion defining a third opening. The pump bulb extends through the first opening, the one or more fluid ports extends through the third opening, and the deflation mode actuator extends through the third opening. The tactile feature includes one or more ridges. The tactile feature includes one or more depressions.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

The penile prosthesis discussed herein includes an outer protective casing that is disposed over a valve body of a pump assembly. The outer protective casing may increase ease of identification of a deflation mode actuator. In some examples, the outer protective casing may reduce the profile of the valve body. Also, the outer protective casing may provide flexibility to adapt the valve body to a variety of shapes and textures to meet the needs of patients. Further, the outer protective casing may protect the valves (and other components associated with the valve body) from grip forces by the patient to prevent valve dislocation or accidental cylinder deflation.

Figure 1B:
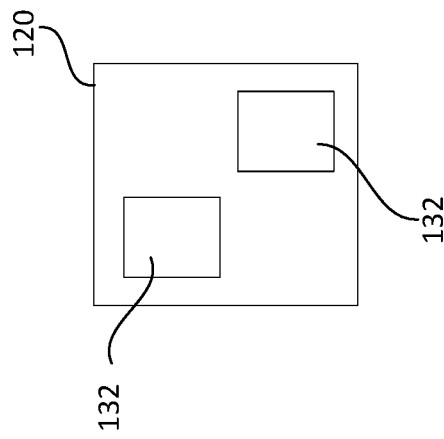
FIG. 1B illustrates an outer protective casing having a tactile feature configured to help a user locate a deflation mode actuator of the pump assembly according to an aspect.
Figure 1A:
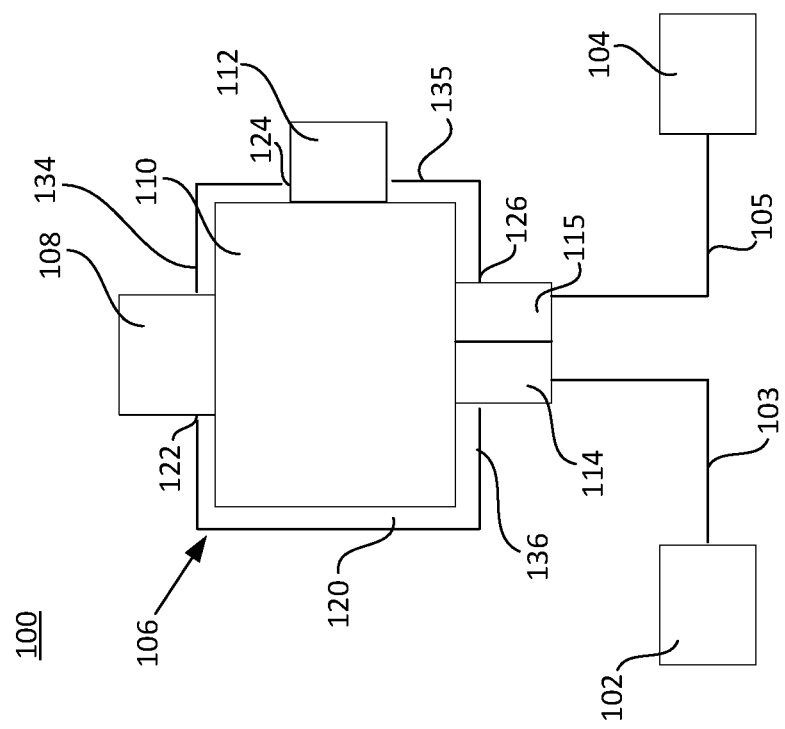
FIG. 1A illustrates an inflatable penile prosthesis having a pump assembly with an outer protective casing according to an aspect.

FIG. 1A illustrates an inflatable penile prosthesis 100 including a fluid reservoir 102, an inflatable member 104, and a pump assembly 106 configured to transfer fluid between the fluid reservoir 102 and the inflatable member 104 according to an aspect. The inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes a pump bulb 108, a valve body 110, a deflation mode actuator 112, and an outer protective casing 120 disposed over the valve body 110. In an inflation mode, the user may operate the pump bulb 108 (e.g., squeeze the pump bulb 108, release, then squeeze again, etc.) to transfer fluid from the fluid reservoir 102 to the pump assembly 106, and from the pump assembly 106 to the inflatable member 104 such that a desired rigidity is achieved in the inflatable member 104. In order to deflate the inflatable member 104, the user may locate the deflation mode actuator 112, and activate the deflation mode actuator 112 to place the inflatable penile prosthesis 100 in a deflation mode.

The deflation mode actuator 112 is movably coupled to the valve body 110. In some examples, the deflation mode actuator 112 includes a protrusion, that when pressed, causes the valve body 110 to define a fluid passageway from the inflatable member 104 to the fluid reservoir 102 in order to deflate the inflatable member 104. In some examples, the deflation mode actuator 112 includes a push rod or button. In some examples, the user presses the deflation mode actuator 112 once (e.g., does not need to hold the deflation mode actuator 112) to cause fluid to drain from the inflatable member 104. In some examples, due to the pressure inside of the inflatable member 104, some of the fluid may be automatically transferred from the inflation member 104 to the fluid reservoir 102 via the pump assembly 106, and then the user may squeeze the inflatable member 104 to transfer some of the remaining fluid in the inflatable member 104.

The valve body 110 includes passageways and valve components such as one or more valves (e.g., inflation valve, refill valve, check valve, ball valve, one-way valve, and/or two-way valve, etc.) and a spool, for example. The valve body 110 may include a silicone material. For example, the valve body 110 may be molded from a silicone material having a medium durometer value.

The pump bulb 108 may be a flexible member defining a cavity. The pump bulb 108 is coupled to and extends from the valve body 110. The pump bulb 108 may be a squeeze pump. In some examples, the pump bulb 108 includes ribbing or dimples to aid the user in gripping the pump bulb 108. The pump bulb 108 may use suction and pressure to move the fluid in and out of the cavity of the pump bulb 108 in the inflation mode. For example, the user may depress or squeeze the pump bulb 108 to expel the fluid out of the cavity, and, when the flexible member returns to its original shape, the resulting suction pushes the fluid into the cavity of the pump bulb 108. In some examples, the pump bulb 108 may have a bulb spring rate that is designed to refill the pump bulb 108 in a selected time frame.

The outer protective casing 120 is configured to protect the valve components of the valve body 110, and assist a user in locating the deflation mode actuator 112 of the inflatable penile prosthesis 100. In some examples, the outer protective casing 120 is a single unitary body that is separate from the valve body 110, but placed over the valve body 110.

As shown in FIG. 1B, the outer protective casing 120 includes tactile features 132 that assist the user in locating the deflation mode actuator 112. In some examples, the tactile features 132 are features that are perceptible by touching the outer protective casing 120. In some examples, the tactile features 132 include one or more protruded (or extended) portions that extend away from a surface of the outer protective casing 120. In some examples, the tactile features 132 include ridges or ribs. In some examples, the tactile features 132 include depressions or recessed portions. In some examples, the tactile features 132 include a combination of ridges and depressions. In some examples, the tactile features 132 include protrusions and grooves. In some examples, the protrusions and grooves are alternatively disposed on one or more surfaces of the outer protective casing 120 (e.g., a first protrusion, then a first groove, then, a second protrusion, then a second groove, etc.). In some examples, the tactile features 132 include bumps. The tactile features 132 are located on one or more of the surfaces of the outer protective casing 120 in order to distinguish the valve body 110 and the pump bulb 108. In some examples, the tactile features 132 are disposed on the outer protective casing 120 at a location proximate (e.g., close to) the deflation mode actuator 112.

The outer protective casing 120 may be an enclosure that surrounds and protects the valve body 110. For example, the outer protective casing 120 may define a cavity that contains the valve body 110. In some examples, at least a portion of the outer protective casing 120 has a shape that conforms to the shape of the valve body 110. In some examples, the outer protective casing 120 includes a polymer material. For example, the outer protective casing 120 is molded from a medical grade polymer. In some examples, the outer protective casing 120 includes a silicon material. For example, the outer protective casing 120 may include a high durometer silicone material that is stiffer than the valve body 110.

The outer protective casing 120 includes a first end portion 134 that defines an opening 122, a second end portion 136 that defines an opening 126, and a sidewall portion 135 that defines an opening 124. The opening 122, the opening 124, and the opening 126 may be separate and distinct openings on different locations on the outer protective casing 120. In some examples, the outer protective casing 120 includes more than three opening. In some examples, the opening 122 and the opening 126 are located on opposite ends of the outer protective casing 120. In some examples, the opening 122 has a shape that is different than a shape of the opening 126. In some examples, the opening 122 has a circular shape. In some examples, the opening 122 has a size (e.g., a diameter) slightly larger than a size (e.g., a diameter) of a portion of the pump bulb 108 that extends from the valve body 110. The pump bulb 108 extends through the opening 122.

The pump assembly 106 includes a reservoir fluid port 114 that extends from the valve body 110. The reservoir fluid port 114 is configured to be coupled to the fluid reservoir 102 (via a first conduit connector 103). For example, the reservoir fluid port 114 is coupled to the first conduit connector 103, and the first conduit connector 103 is coupled to the fluid reservoir 102. In some examples, the reservoir fluid port 114 includes a tubular member defining a cavity that is fluidly connected to the valve body 110. The pump assembly 106 includes one or more cylinder fluid ports 115 that extend from the valve body 110, and are fluidly coupled to the inflatable member 104 (via a second conduit connector 105). In some examples, the one or more cylinder fluid ports 115 includes a first cylinder fluid port configured to be fluidly coupled to a first cylinder of the inflatable member 104 (via the second conduit connector 105), and a second cylinder fluid port configured to be fluidly coupled to a second cylinder of the inflatable member 104 (via the second conduit connector 105). For example, the cylinder fluid ports 115 are configured to be coupled to the second conduit connector 105, and the second conduit connector 105 is configured to be coupled to the inflatable member 104. In some examples, the cylinder fluid ports 115 include tubular members that define cavities fluidly connected to the valve body 110.

The opening 126 is slightly larger than a collective size of the reservoir fluid port 114 and the one or more cylinder fluid ports 115. The reservoir fluid port 114 and the one or more cylinder fluid ports 115 extend through the opening 126. The opening 124 is disposed on the sidewall portion 135 of the outer protection casing 120 between the first end portion 134 and the second end portion 136. The opening 124 has a size that is slightly larger than a size of the deflation mode actuator 112. In some examples, the opening 124 has a circular shape. However, the shape of the opening 124 may depend on the shape of the deflation mode actuator 112. The deflation mode actuator 112 extends through the opening 124.

Each of the first conduit connector 103 and the second conduit connector 105 may define a lumen configured to transfer the fluid to and from the pump assembly 106. The first conduit connector 103 may be coupled to the pump assembly 106 and the fluid reservoir 102 such that fluid can be transferred between the pump assembly 106 and the fluid reservoir 102 via the first conduit connector 103. For example, the first conduit connector 103 may define a first lumen configured to transfer fluid between the pump assembly 106 and the fluid reservoir 102. The first conduit connector 103 may include a single or multiple tube members for transferring the fluid between the pump assembly 106 and the fluid reservoir 102.

The second conduit connector 105 may be coupled to the pump assembly 106 and the inflatable member 104 such that fluid can be transferred between the pump assembly 106 and the inflatable member 104 via the second conduit connector 105. For example, the second conduit connector 105 may define a second lumen configured to transfer fluid between the pump assembly 106 and the inflatable member 104. The second conduit connector 105 may include a single or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The fluid reservoir 102 may include a container having an internal chamber configured to hold or house fluid that is used to inflate the inflatable member 104. The volumetric capacity of the fluid reservoir 102 may vary depending on the size of the inflatable penile prosthesis 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

Figure 2:
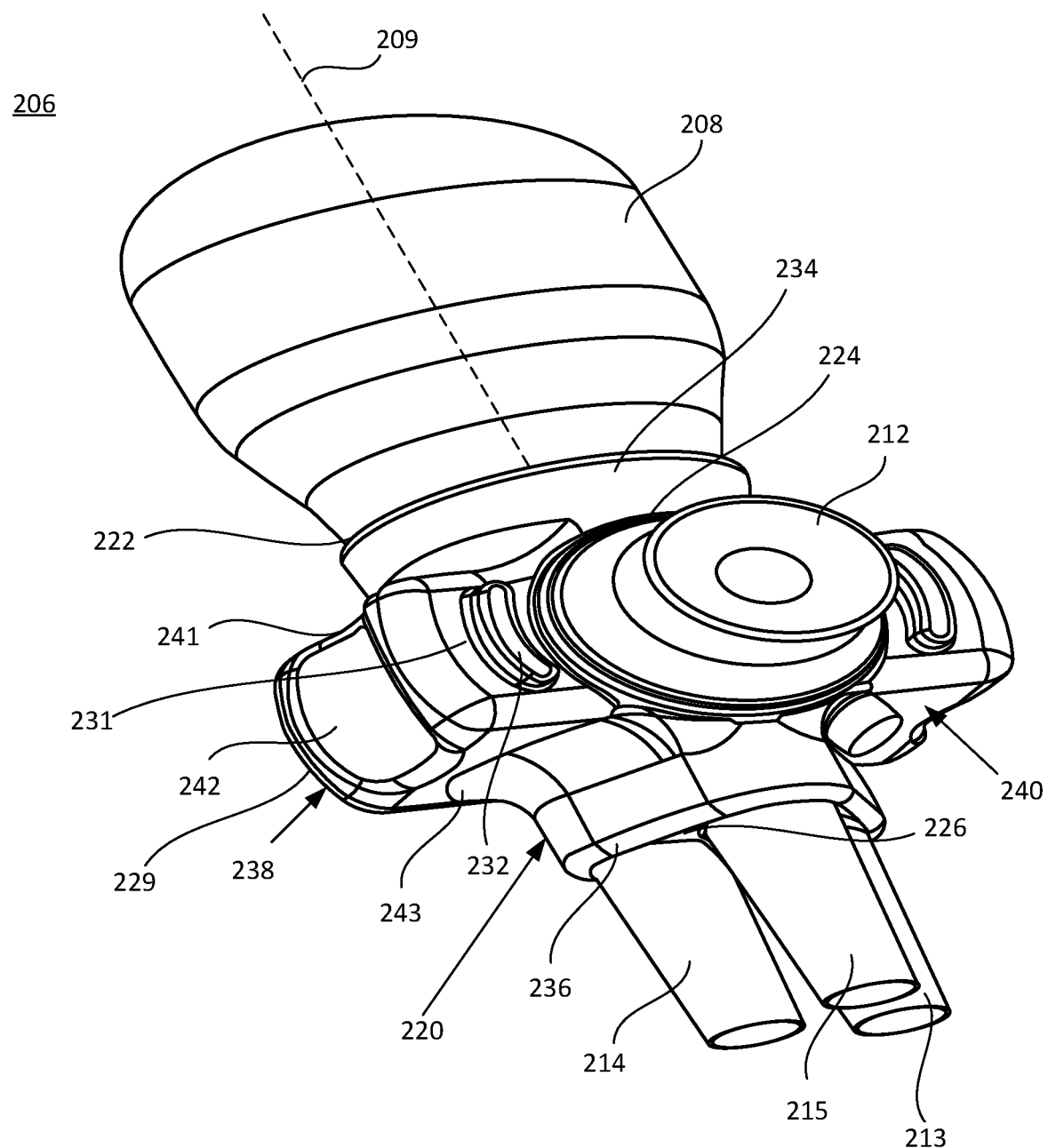
FIG. 2 illustrates a pump assembly having an outer protective casing disposed over a valve body according to an aspect.

FIG. 2 illustrates a pump assembly 206 having an outer protective casing 220 disposed over a valve body according to an aspect. The pump assembly 206 may include any of the features described with reference to the pump assembly 106 of FIG. 1A, and the outer protective casing 220 may include any of the features described with reference to the outer protective casing 120 of FIGS. 1A and 1B. In addition, the pump assembly 106 of FIG. 1A and/or the outer protective casing 120 of FIGS. 1A and 1B may include any of the features described with reference to the pump assembly 206 of FIG. 2.

The pump assembly 206 includes a pump bulb 208, a valve body (not shown in FIG. 2 because it is covered by the outer protective casing 220), a deflation mode actuator 212, the outer protective casing 220, and fluid ports such as a first cylinder fluid port 213, a second cylinder fluid port 215, and a reservoir fluid port 214. The reservoir fluid port 214 is configured to be connected to the first conduit connector 103 of FIG. 1, and the first cylinder fluid port 213 and the second cylinder fluid port 215 are configured to be connected to the second conduit connector 105 of FIG. 1. The first cylinder fluid port 213 includes a first tubular member defining a cavity, and the first tubular member is coupled to the valve body. The second cylinder fluid port 215 include includes a second tubular member defining a cavity, and the second tubular member is coupled to the valve body. The reservoir fluid port 214 includes a third tubular member defining a cavity, and the third tubular member is coupled to the valve body. In some examples, the first tubular member, the second tubular member, and the third tubular member are disposed parallel to each other.

As shown in FIG. 2, the outer protective casing 220 may be a single unitary body (e.g., a single piece) that defines an internal cavity, and the valve body is disposed within the internal cavity of the outer protective casing 220. The outer protective casing 220 may be an enclosure that surrounds and protects the valve body. In some examples, at least a portion of the outer protective casing 220 has a shape that conforms to the shape of the valve body.

The outer protective casing 220 includes a first end portion 234 that defines an opening 222, and a second end portion 236 that defines an opening 226. The opening 222 and the opening 226 are disposed on opposite ends of the outer protective casing 220. In some examples, the opening 222 is circular. In some examples, the opening 226 has a different shape than the opening 222. In some examples, the opening 226 has a non-circular shape. The pump bulb 208 extends from the opening 222, and the fluid ports (e.g., the first cylinder fluid port 213, the second cylinder fluid port 215, and the reservoir fluid port 214) extend from the opening 226. The opening 222 may have a size (e.g., a diameter) slightly larger than a size (e.g., a diameter) of a portion of the pump bulb 208 that extends from the valve body. In some examples, the first end portion 234 covers a portion of the pump bulb 208. The opening 226 may have a size that is slightly larger than the collective size of the first cylinder fluid port 213, the second cylinder fluid port 215, and the reservoir fluid port 214.

The outer protective casing 220 defines an opening 224. The deflation mode actuator 212 extends through the opening 224. In some examples, the opening 224 is circular. The opening 224 has a size (e.g., a diameter) that is slightly larger than a size of the deflation mode actuator 212. In some examples, the opening 224 is located on a side portion of the outer protective casing 220 at a location between the first end portion 234 and the second end portion 236. In some examples, the deflation mode actuator 212 extends in a direction that is orthogonal to a longitudinal axis 209 of the pump bulb 208.

The outer protective casing 220 includes a first protruded side portion 238, and a second protruded side portion 240. The first protruded side portion 238 extends in a first direction (e.g., orthogonal to the longitudinal axis 209 of the pump bulb 208), and the second protruded side portion 240 extending in a second direction (e.g., orthogonal to longitudinal axis 209 of the pump bulb 208), where the second direction is opposite to the first direction. In some examples, the opening 224 is disposed between the first protruded side portion 238 and the second protruded side portion 240.

The first protruded side portion 238 has a three-dimensional shape, where one or more of its surfaces define one or more tactile features configured to assist a user to locate the deflation mode actuator 212. The second protruded side portion 240 may have a three-dimensional shape, where one or more of its surfaces define one or more tactile features configured to assist the user to locate the deflation mode actuator 212.

The first protruded side portion 238 includes a surface 241, and a surface 243 disposed opposite to the surface 241. In some examples, the surface 241 is curved (e.g., a concave surface). In some examples, the surface 243 is curved (e.g., a concave surface). In some examples, the surface 241 and/or the surface 243 is devoid of surface tactile features (e.g., bumps, ridges, depressions, etc.). In some examples, the surface 241 and/or the surface 243 are smooth. The first protruded side portion 238 includes an outer surface 242 between the surface 241 and the surface 243. In some examples, the outer surface 242 includes a concave portion. In some examples, the outer surface 242 defines a depression or a recessed portion. In some examples, the depression defined by the outer surface 242 is a tactile feature that help the user locate the deflation mode actuator 212.

The first protruded side portion 238 includes a surface 229 and a surface 231 disposed opposite to the surface 229. The surface 231 may be disposed adjacent to the opening 224 (e.g., disposed in a plane that also includes the opening 224). The surface 231 may include a ridge 232. The ridge 232 is disposed on a location on the surface 231 that is proximate to the deflation mode actuator 212. In some examples, the ridge 232 is an elongated raised member. In some examples, the ridge 232 is curved. The ridge 232 is located proximate to the deflation mode actuator 212. Since the second protruded side portion 240 may include the same features as the first protruded side portion 238, the details of the second protruded side portion 340 are omitted for the same of brevity.

Figure 3:
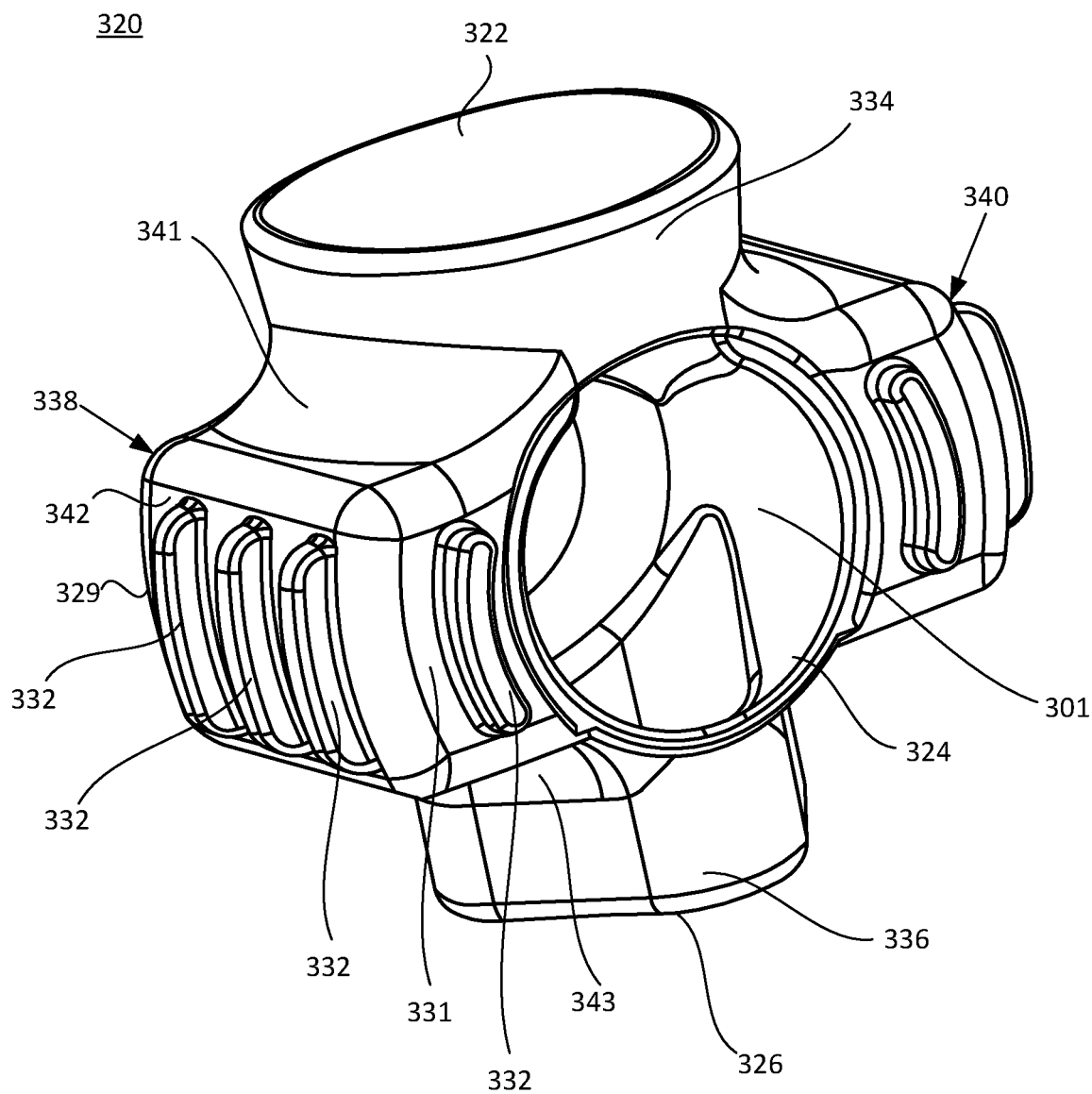
FIG. 3 illustrates an outer protective casing according to an aspect.

FIG. 3 illustrates an outer protective casing 320 according to another aspect. The outer protective casing 320 may include any of the features discussed with reference to the outer protective casing 120 of FIGS. 1A and 1B and the outer protective casing 220 of FIG. 2. In addition, in some examples, the outer protective casing 120 of FIGS. 1A and 1B and/or the outer protective casing 220 of FIG. 2 may include any of the features discussed with reference to the outer protective casing 320 of FIG. 3.

The outer protective casing 320 includes a cavity 301 that is configured to hold a valve body of a pump assembly of a penile prosthesis. The outer protective casing 320 includes a first end portion 334 that defines an opening 322 (where a pump bulb extends through), and a second end portion 336 that defines an opening 326 (where fluid ports extends through). Also, the outer protective casing 320 defines an opening 324 between the first end portion 334 and the second end portion 336. A deflation mode actuator may extend through the opening 324.

The outer protective casing 320 includes a first protruded side portion 338 that extends from one side of the outer protective casing 320, and a second protruded side portion 340 that extends from the other side of the outer protective casing 320. The opening 324 may be disposed between the first protruded side portion 338 and the second protruded side portion 340. The first protruded side portion 338 may have a three-dimensional shape, where one or more of its surfaces define one or more tactile features configured to assist the user to locate the deflation mode actuator. In some examples, the first protruded side portion 338 includes one or more ridges 332 on at least two of its surfaces, where each ridge 332 is an elongated raised member.

The first protruded side portion 338 includes a surface 341, and a surface 343 disposed opposite to the surface 341. In some examples, the surface 341 is curved (e.g., a concave surface). In some examples, the surface 343 is curved (e.g., a concave surface). In some examples, the surface 341 and/or the surface 343 are devoid of surface tactile features. In some examples, the surface 341 and/or the surface 343 are smooth. The first protruded side portion 338 includes an outer surface 342 that extends between the surface 341 and the surface 343. In some examples, the outer surface 342 includes a plurality of the ridges 332. In some examples, each ridge 332 on the outer surface 342 is an elongated raised member, and the ridges 332 are arranged parallel to each other. In some examples, the elongated raised member is a linear member. The first protruded side portion 338 includes a surface 329 and a surface 331 disposed opposite to the surface 329. The surface 331 may be disposed adjacent to the opening 324 (e.g., disposed in a plane that also includes the opening 324). The surface 331 may include one or more ridges 332. In some examples, the surface 331 has a single ridge 332. In some examples, the ridge 332 on the surface 331 is an elongated raised elongated member that includes a curved portion. Since the second protruded side portion 340 may include the same features as the first protruded side portion 338, the details of the second protruded side portion 340 are omitted for the same of brevity.

Figure 4:
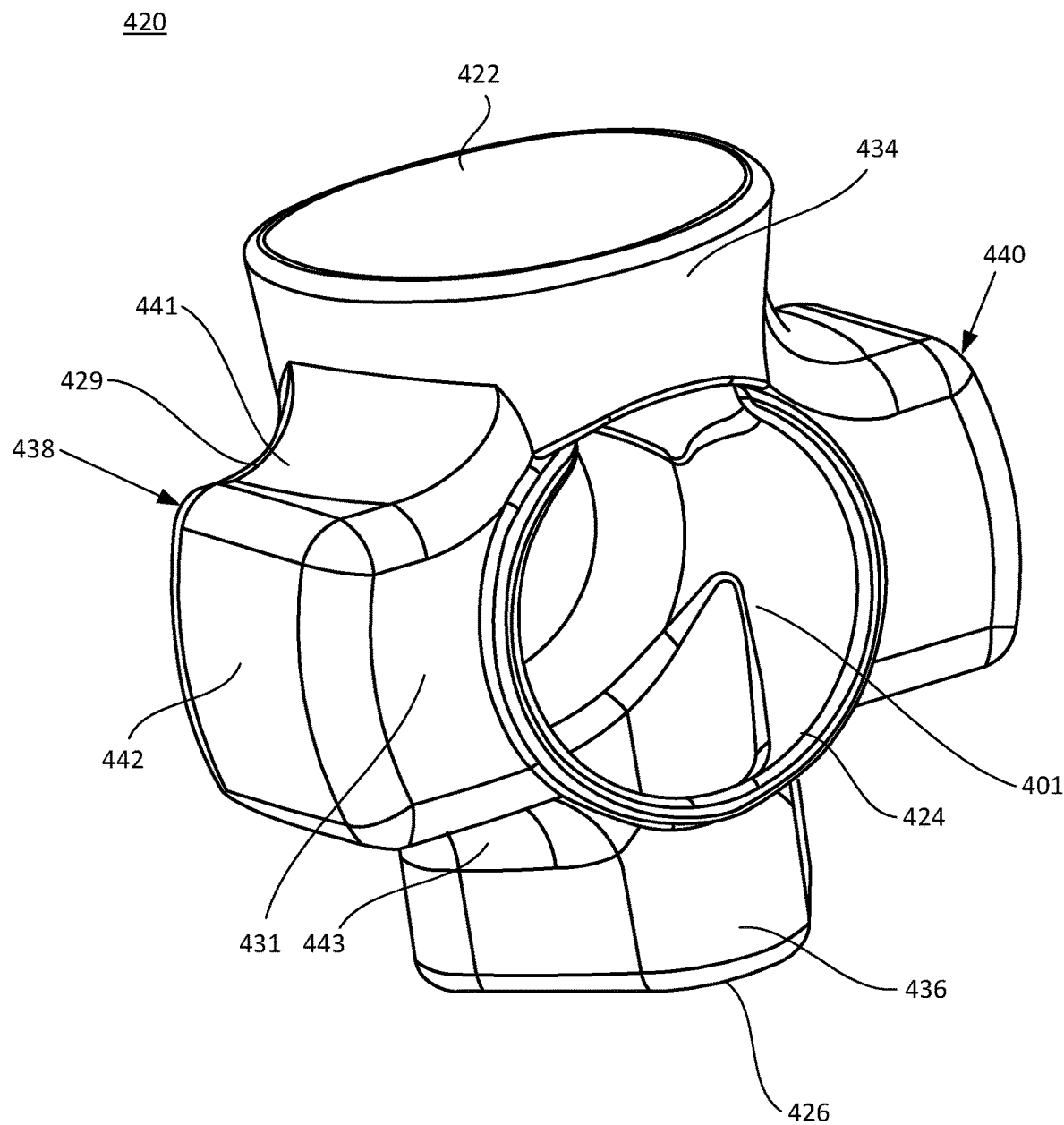
FIG. 4 illustrates an outer protective casing according to an aspect.

FIG. 4 illustrates an outer protective casing according to another aspect. The outer protective casing 420 may include any of the features discussed with reference to the outer protective casing 120 of FIGS. 1A and 1B, the outer protective casing 220 of FIG. 2, and the outer protective casing 320 of FIG. 3. In addition, in some examples, the outer protective casing 120 of FIGS. 1A and 1B, the outer protective casing 220 of FIG. 3, and/or the outer protective casing 320 of FIG. 3 may include any of the features discussed with reference to the outer protective casing 420 of FIG. 4.

The outer protective casing 420 includes a first protruded side portion 438 and a second protruded side portion 440. In the example of FIG. 4, the first protruded side portion 438 is devoid of a ridge, and the second protruded side portion 440 is devoid of a ridge. Rather, the first and second protruded side portions 438, 440 themselves may be used as tactile features that enable the user to locate a deflation mode actuator.

The outer protective casing 420 includes a cavity 401 that is configured to hold a valve body of a pump assembly of a penile prosthesis. The outer protective casing 420 includes a first end portion 434 that defines an opening 422 (where a pump bulb extends through), and a second end portion 436 that defines an opening 426 (where fluid ports extends through). Also, the outer protective casing 420 defines an opening 424 between the first end portion 434 and the second end portion 436. The deflation mode actuator of the pump assembly may extend through the opening 424.

The opening 424 may be disposed between the first protruded side portion 438 and the second protruded side portion 440. The first protruded side portion 438 may have a three-dimensional shape, and the second protruded side portion 440 may have a three-dimensional shape, which may assist the user to locate the deflation mode actuator. For example, the first protruded side portion 438 includes a surface 441, and a surface 443 disposed opposite to the surface 441. In some examples, the surface 441 is curved (e.g., a concave surface). In some examples, the surface 443 is curved (e.g., a concave surface). In some examples, the surface 441 and the surface 443 have the same curvature. In some examples, the surface 441 and/or the surface 443 are devoid of surface tactile features. In some examples, the surface 441 and/or the surface 443 are smooth.

The first protruded side portion 438 includes an outer surface 442 that extends between the surface 441 and the surface 443. In some examples, the outer surface 442 is devoid of surface tactile features. In some examples, the outer surface 442 defines a depression. In some examples, the outer surface 442 is devoid of a depression. In some examples, the outer surface 442 is smooth. The first protruded side portion 438 includes a surface 429 and a surface 431 disposed opposite to the surface 429. The surface 431 may be disposed adjacent to the opening 424 (e.g., disposed in a plane that also includes the opening 424). In some examples, the surface 431 is devoid of a ridge. In some examples, the surface 431 is smooth. Since the second protruded side portion 440 may include the same features as the first protruded side portion 438, the details of the second protruded side portion 440 are omitted for the same of brevity.

Figure 5:
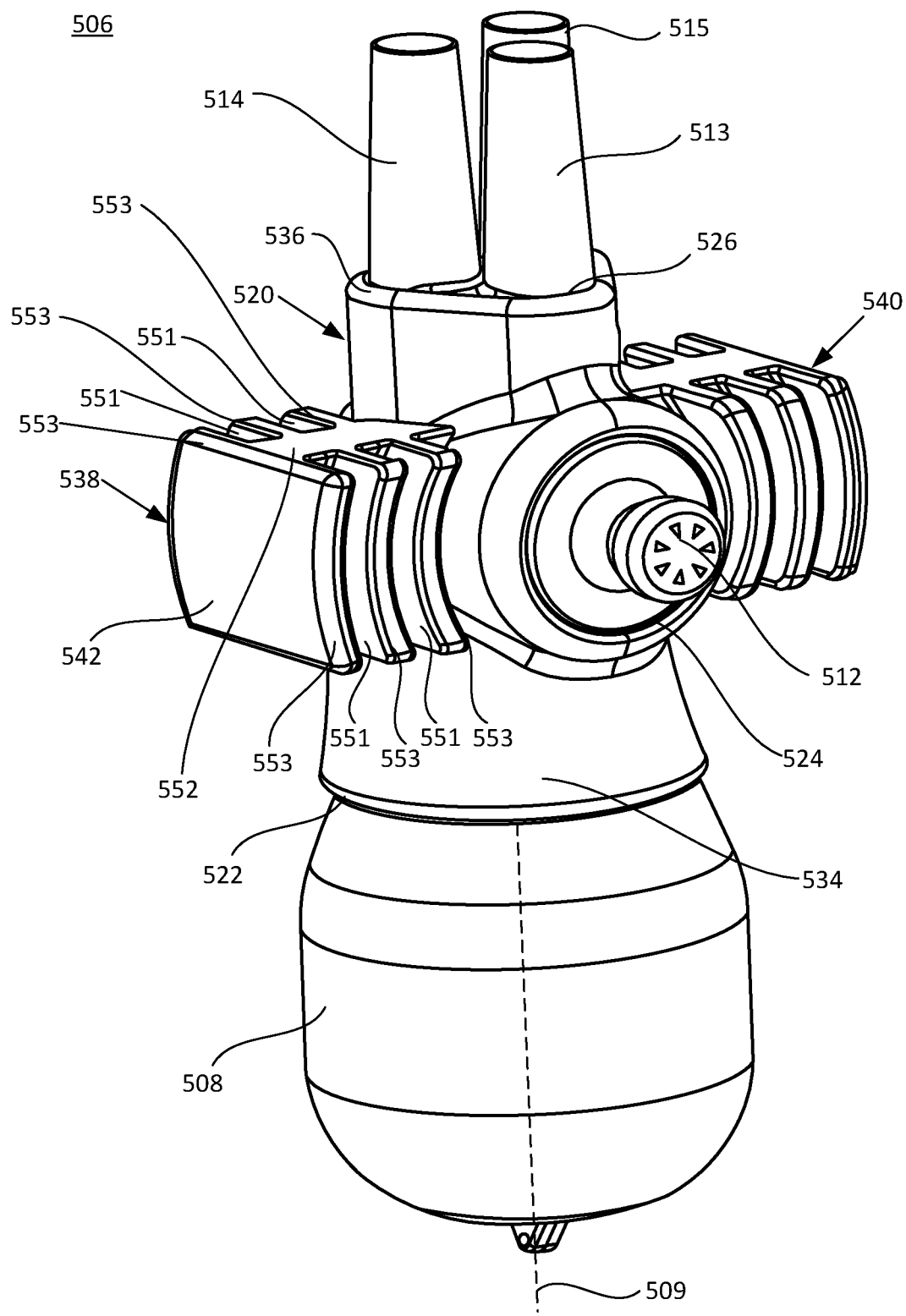
FIG. 5 illustrates a pump assembly having an outer protective casing disposed over a valve body according to an aspect.

FIG. 5 illustrates a pump assembly 506 having an outer protective casing 520 disposed over a valve body according to an aspect. The pump assembly 506 may include any of the features described with reference to the pump assembly 506 of FIG. 1A, the outer protective casing 520 may include any of the features described with reference to the outer protective casing 120 of FIGS. 1A and 1B, the pump assembly 206 of FIG. 2, the outer protective casing 320 of FIG. 3, and/or the outer protective casing 420 of FIG. 4. In addition, the pump assembly 106 of FIG. 1A, the outer protective casing 120 of FIGS. 1A and 1B, the pump assembly 206 of FIG. 2, the outer protective casing 320 of FIG. 3, the outer protective casing 420 of FIG. 4 may include any of the features described with reference to the pump assembly 506 of FIG. 2.

The pump assembly 506 includes a pump bulb 508, a valve body (not shown in FIG. 5 because it is covered by the outer protective casing 520), a deflation mode actuator 512, the outer protective casing 520, and fluid ports such as a first cylinder fluid port 513, a second cylinder fluid port 515, and a reservoir fluid port 514. The reservoir fluid port 514 is configured to be connected to the first conduit connector 103 of FIG. 1, and the first cylinder fluid port 513 and the second cylinder fluid port 515 are configured to be connected to the second conduit connector 105 of FIG. 1.

The outer protective casing 520 includes a first end portion 534 that defines an opening 522, and a second end portion 536 that defines an opening 526. The opening 522 and the opening 526 are disposed on opposite ends of the outer protective casing 520. The pump bulb 508 extends from the opening 522, and the fluid ports (e.g., the first cylinder fluid port 513, the second cylinder fluid port 515, and the reservoir fluid port 514) extend from the opening 526. The opening 522 may have a size (e.g., a diameter) slightly larger than a size (e.g., a diameter) of a portion of the pump bulb 508 that extends from the valve body. The opening 526 may have a size that is slightly larger than the collective size of the first cylinder fluid port 513, the second cylinder fluid port 515, and the reservoir fluid port 514.

The outer protective casing 520 defines an opening 524. The deflation mode actuator 512 may extend through the opening 524. The opening 524 has a size (e.g., a diameter) that is slightly larger than a size of the deflation mode actuator 512. In some examples, the opening 524 is located on a side portion of the outer protective casing 520 at a location between the first end portion 534 and the second end portion 536. In some examples, the deflation mode actuator 512 extends in a direction that is orthogonal to a longitudinal axis 509 of the pump bulb 508.

The outer protective casing 520 includes a first protruded side portion 538, and a second protruded side portion 540. The first protruded side portion 538 extends in a first direction (e.g., orthogonal to the longitudinal axis 509 of the pump bulb 508), and the second protruded side portion 540 extending in a second direction (e.g., orthogonal to longitudinal axis 509 of the pump bulb 508), where the second direction is opposite to the first direction. In some examples, the deflation mode actuator 512 extends in a direction orthogonal to the first protruded side portion 538 and the second protruded side portion 540. In some examples, the opening 524 is disposed between the first protruded side portion 538 and the second protruded side portion 540.

The first protruded side portion 538 has a three-dimensional shape, where one or more of its surfaces define one or more tactile features configured to assist a user to locate the deflation mode actuator 512. The second protruded side portion 540 may have a three-dimensional shape, where one or more of its surfaces define one or more tactile features configured to assist the user to locate the deflation mode actuator 512.

The first protruded side portion 538 includes an outer surface 542, protrusions 553, and grooves 551 configured to assist the user to locate the deflation mode actuator 512. For example, the first protruded side portion 538 includes a central portion 552, and a plurality of spaced-apart protrusions 553 extend from one side of the central portion 552, and a plurality of spaced-part protrusions 553 extend from the other side of the central portion 552. A particular groove 551 is disposed between adjacent protrusions 553. In some examples, the protrusions 553 include curved portions. In some examples, the number of protrusions 553 on each side of the central portion 552 is three. In some examples, the number of protrusions 553 on each side of the central portion 552 is more than three. The protrusions 553 may extend in a direction parallel to the deflation mode actuator 512. Since the second protruded side portion 540 may include the same features as the first protruded side portion 538, the details of the second protruded side portion 540 are omitted for the same of brevity.

Figure 6:
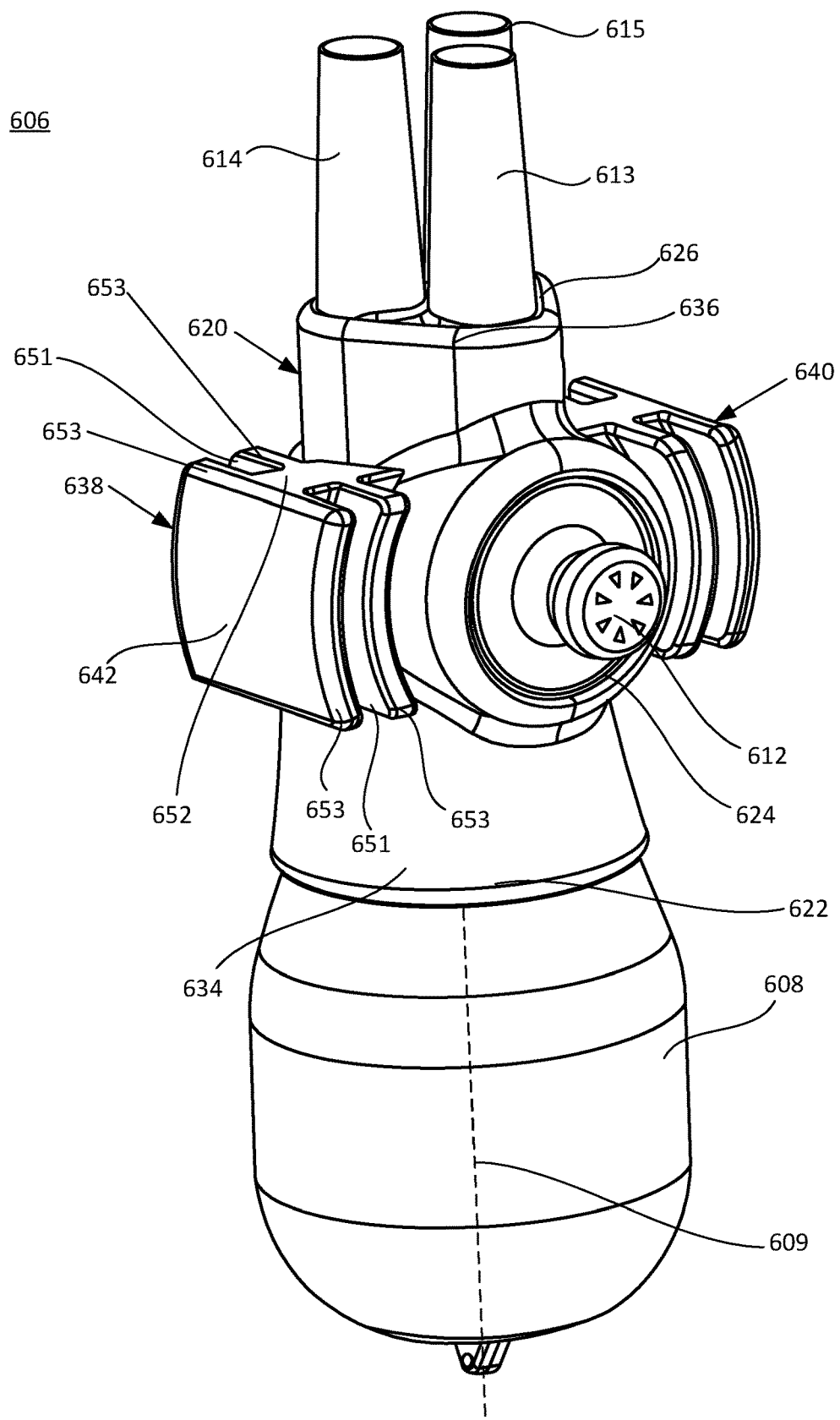
FIG. 6 illustrates a pump assembly having an outer protective casing disposed over a valve body according to an aspect.

FIG. 6 illustrates a pump assembly 606 having an outer protective casing 620 disposed over a valve body according to an aspect. The pump assembly 606 may include any of the features described with reference to the previous figures. In addition, the pump assembly 106 of FIG. 1A, the pump assembly 206, the outer protective casing 320 of FIG. 3, the outer protective casing 420 of FIG. 4, and/or the pump assembly 506 of FIG. 5 may include any of the features described with reference to the pump assembly 606 of FIG. 6. The pump assembly 606 may be similar to the pump assembly 506 of FIG. 5 except that first and second protruded side portions 638, 640 include two protrusions 653.

The pump assembly 606 includes a pump bulb 608, a valve body (not shown in FIG. 6 because it is covered by the outer protective casing 620), a deflation mode actuator 612, the outer protective casing 620, and fluid ports such as a first cylinder fluid port 613, a second cylinder fluid port 615, and a reservoir port 614. The outer protective casing 620 includes a first end portion 634 that defines an opening 622, and a second end portion 636 that defines an opening 626. The pump bulb 608 extends from the opening 622, and the fluid ports extend from the opening 626.

The outer protective casing 620 defines an opening 624. The deflation mode actuator 612 extends through the opening 624. In some examples, the opening 624 is located on a side portion of the outer protective casing 620 at a location between the first end portion 634 and the second end portion 636. In some examples, the deflation mode actuator 612 extends in a direction that is orthogonal to a longitudinal axis 609 of the pump bulb 608. The outer protective casing 620 includes a first protruded side portion 638, and a second protruded side portion 640. The first protruded side portion 638 extends in a first direction (e.g., orthogonal to the longitudinal axis 609 of the pump bulb 608), and the second protruded side portion 640 extending in a second direction (e.g., orthogonal to longitudinal axis 609 of the pump bulb 608), where the second direction is opposite to the first direction. In some examples, the deflation mode actuator 612 extends in a direction orthogonal to the first protruded side portion 638 and the second protruded side portion 640. In some examples, the opening 624 is disposed between the first protruded side portion 638 and the second protruded side portion 640.

The first protruded side portion 638 has a three-dimensional shape, where one or more of its surfaces define one or more tactile features configured to assist a user to locate the deflation mode actuator 612. The second protruded side portion 640 may have a three-dimensional shape, where one or more of its surfaces define one or more tactile features configured to assist the user to locate the deflation mode actuator 612.

The first protruded side portion 638 includes an outer surface 642, protrusions 653, and grooves 651 configured to assist the user to locate the deflation mode actuator 512. For example, the first protruded side portion 638 includes a central portion 652, and a plurality of spaced-apart protrusions 653 extend from one side of the central portion 652, and a plurality of spaced-part protrusions 653 extend from the other side of the central portion 652. A particular groove 651 is disposed between adjacent protrusions 653. In some examples, the protrusions 653 are curved. In some examples, the number of protrusions 653 on each side of the central portion 652 is two. In some examples, the number of protrusions 653 on each side of the central portion 652 is less than two. The protrusions 653 may extend in a direction parallel to the deflation mode actuator 612. Since the second protruded side portion 640 may include the same features as the first protruded side portion 638, the details of the second protruded side portion 640 are omitted for the same of brevity.

Figure 7:
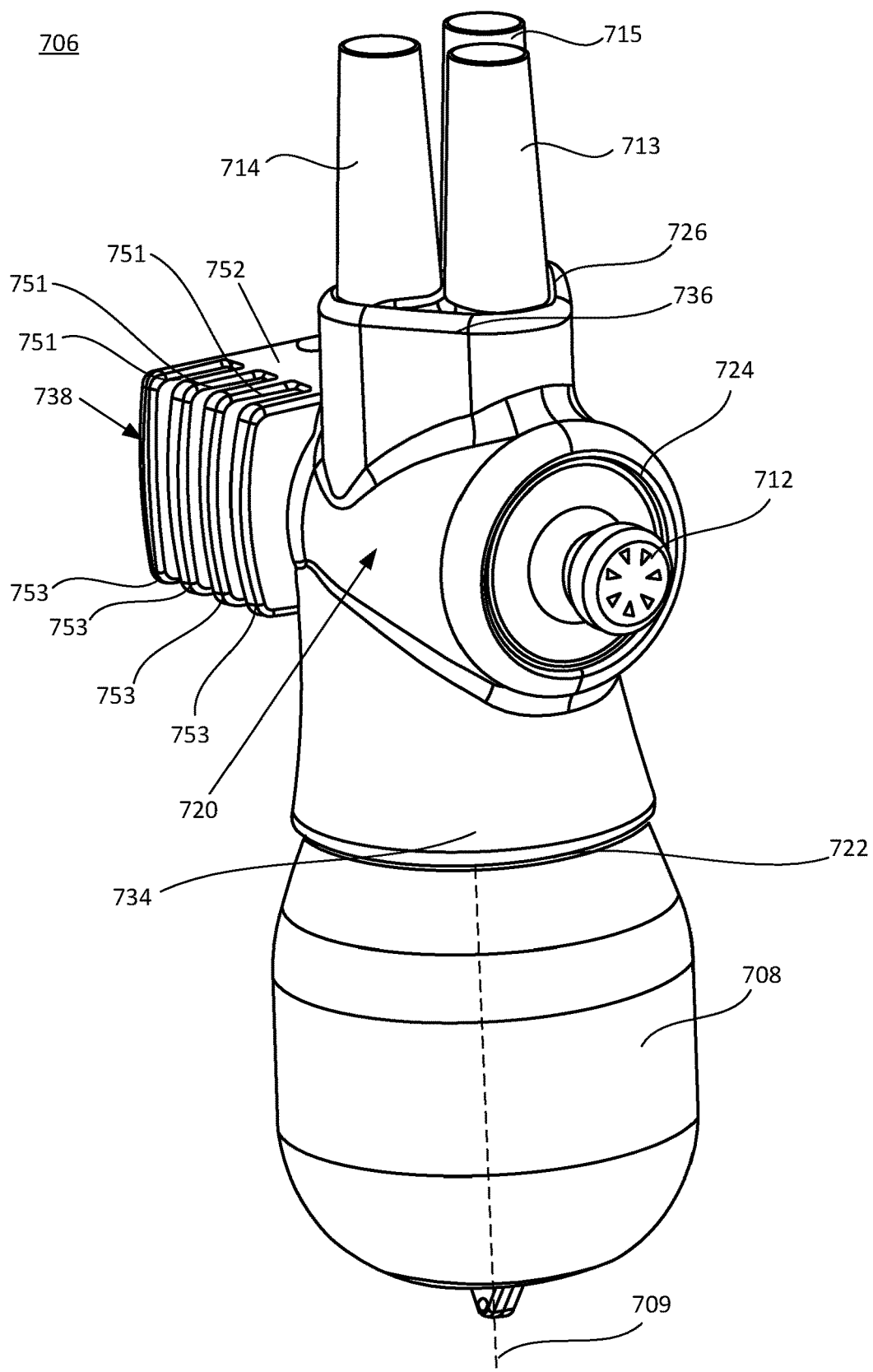
FIG. 7 illustrates a pump assembly having an outer protective casing disposed over a valve body according to an aspect.

FIG. 7 illustrates a pump assembly 706 having an outer protective casing 720 disposed over a valve body according to an aspect. The pump assembly 706 may include any of the features described with reference to the previous figures. In addition, the pump assembly 106 of FIG. 1A, the pump assembly 206, the outer protective casing 320 of FIG. 3, the outer protective casing 420 of FIG. 4, the pump assembly 506 of FIG. 5, and/or the pump assembly 606 of FIG. 6 may include any of the features described with reference to the pump assembly 706 of FIG. 7. The pump assembly 706 may be similar to the pump assembly 506 of FIG. 5 except that the outer protective casing 720 includes a single protruded side portion 738 that extends from a location on the outer protective casing 720 that is opposite to a deflation mode actuator 712.

The pump assembly 706 includes a pump bulb 708, a valve body (not shown in FIG. 7 because it is covered by the outer protective casing 720), the deflation mode actuator 712, the outer protective casing 720, and fluid ports such as a first cylinder fluid port 713, a second cylinder fluid port 715, and a reservoir port 714. The outer protective casing 720 includes a first end portion 734 that defines an opening 722, and a second end portion 736 that defines an opening 726. The pump bulb 708 extends from the opening 722, and the fluid ports extend from the opening 726.

The outer protective casing 720 defines an opening 724. The deflation mode actuator 712 extends through the opening 724. In some examples, the opening 724 is located on a first side portion of the outer protective casing 720 at a location between the first end portion 734 and the second end portion 736. In some examples, the deflation mode actuator 712 extends in a direction that is orthogonal to a longitudinal axis 709 of the pump bulb 708. The protruded side portion 738 extends from a second side portion of the outer protective casing 720 at a location between the first end portion 734 and the second end portion 736, where the second side portion is opposite to the first side portion. The protruded side portion 738 may extend in a direction opposite to the deflation mode actuator 712.

The protruded side portion 738 includes protrusions 753 and grooves 751 configured to assist the user to locate the deflation mode actuator 712. For example, the protruded side portion 738 includes a central portion 752, and a plurality of spaced-apart protrusions 753 extend from one side of the central portion 752, and a plurality of spaced-part protrusions 753 extend from the other side of the central portion 752. A particular groove 751 is disposed between adjacent protrusions 753. In some examples, the protrusions 753 include curved portions. The protrusions 753 may extend in a direction orthogonal to the deflation mode actuator 712.

Figure 8:
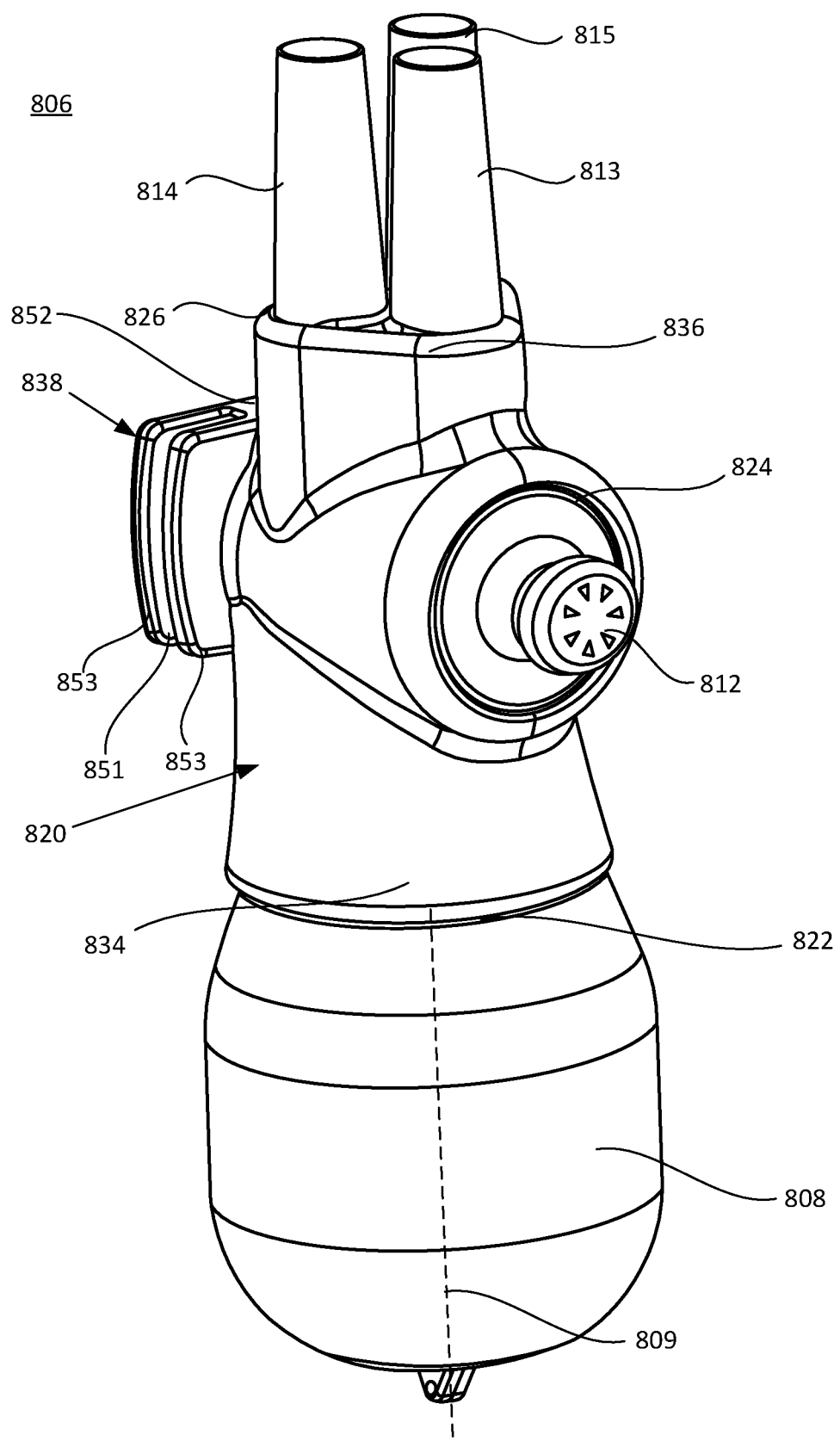
FIG. 8 illustrates a pump assembly having an outer protective casing disposed over a valve body according to an aspect.

FIG. 8 illustrates a pump assembly 806 having an outer protective casing 820 disposed over a valve body according to an aspect. The pump assembly 806 may include any of the features described with reference to the previous figures. In addition, the pump assembly 106 of FIG. 1A, the pump assembly 206, the outer protective casing 320 of FIG. 3, the outer protective casing 420 of FIG. 4, the pump assembly 506 of FIG. 5, the pump assembly 606 of FIG. 6, and/or the pump assembly 706 of FIG. 7 may include any of the features described with reference to the pump assembly 806 of FIG. 8. The pump assembly 806 may be similar to the pump assembly 706 of FIG. 7 except that the protruded side portion 838 includes two protrusions 653. For example, the protruded side portion 838 has a smaller length than a length of the protruded side portion 738 of FIG. 7.

The pump assembly 806 includes a pump bulb 808, a valve body (not shown in FIG. 8 because it is covered by the outer protective casing 820), a deflation mode actuator 812, the outer protective casing 820, and fluid ports such as a first cylinder fluid port 813, a second cylinder fluid port 815, and a reservoir port 814. The outer protective casing 820 includes a first end portion 834 that defines an opening 822, and a second end portion 836 that defines an opening 826. The pump bulb 808 extends from the opening 822, and the fluid ports extend from the opening 826.

The outer protective casing 820 defines an opening 824. The deflation mode actuator 812 extends through the opening 824. In some examples, the opening 824 is located on a first side portion of the outer protective casing 820 at a location between the first end portion 834 and the second end portion 836. In some examples, the deflation mode actuator 812 extends in a direction that is orthogonal to a longitudinal axis 809 of the pump bulb 808. The protruded side portion 838 extends from a second side portion of the outer protective casing 820 at a location between the first end portion 834 and the second end portion 836, where the second side portion is opposite to the first side portion. The protruded side portion 838 may extend in a direction opposite to the deflation mode actuator 812.

The protruded side portion 838 includes protrusions 853 and grooves 851 configured to assist the user to locate the deflation mode actuator 812. For example, the protruded side portion 838 includes a central portion 852, and spaced-apart protrusions 853 that extend from one side of the central portion 852, and spaced-part protrusions 853 that extend from the other side of the central portion 852. A groove 851 is disposed between adjacent protrusions 853. In some examples, the protrusions 853 are curved. The protrusions 853 may extend in a direction orthogonal to the deflation mode actuator 812.

Figure 9:
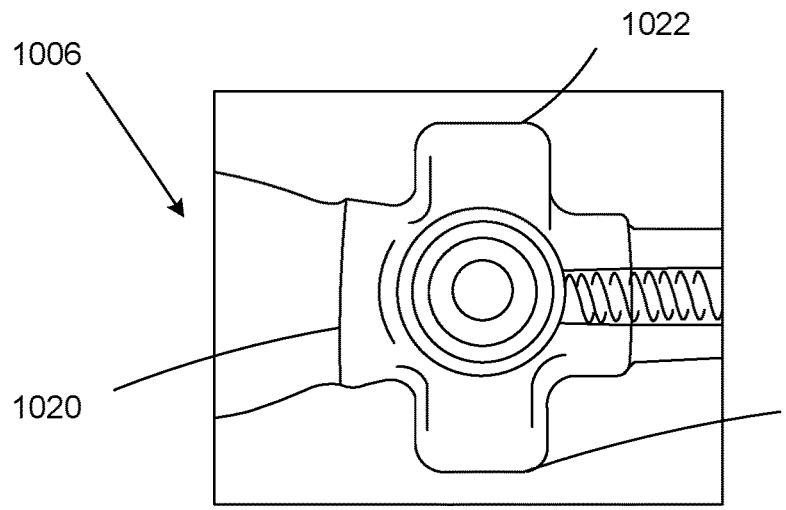
FIGS. 9-48 illustrate pump assemblies having outer protective casings according to various aspects.
Figure 10:
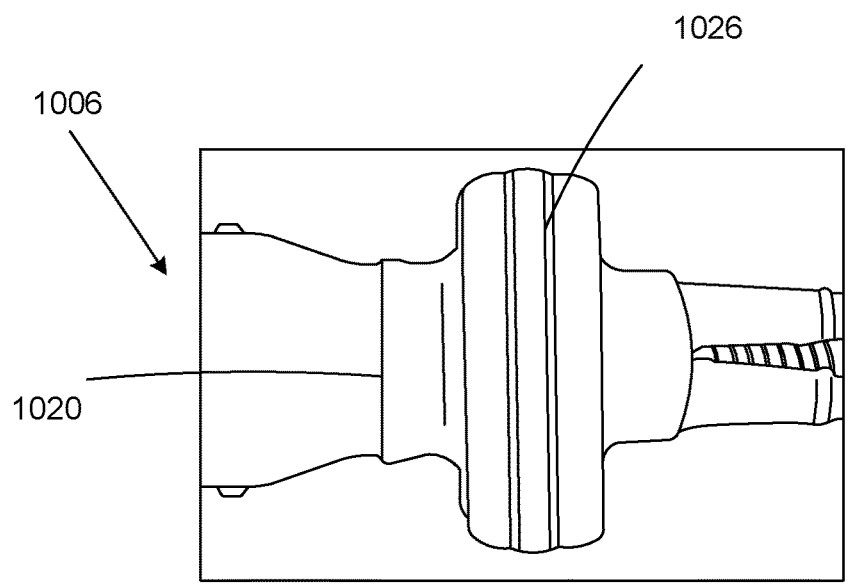
Figure 11:
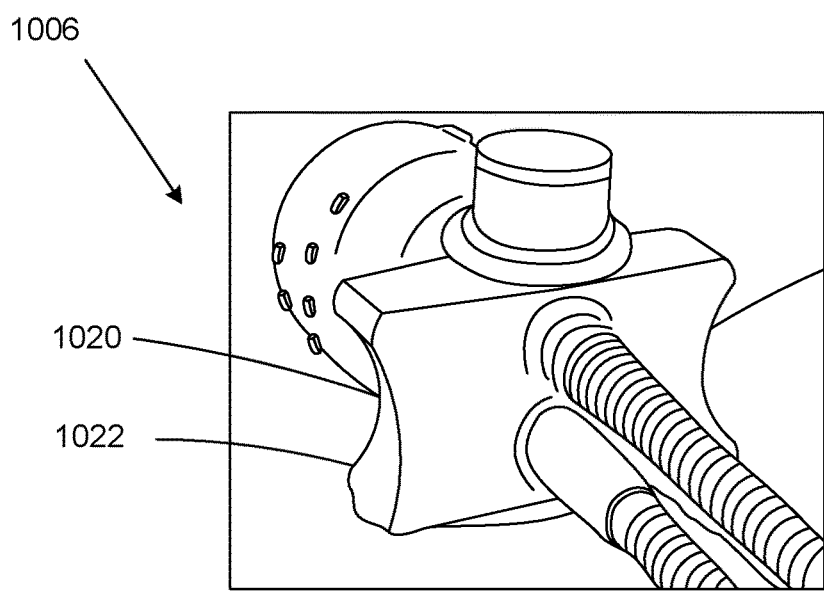

FIG. 9 is a top view of a pump assembly 1006. FIG. 10 is a bottom view of the pump assembly 1006. FIG. 11 is a perspective view of the pump assembly 1006. The pump assembly 1006 has an outer protective casing 1020 disposed over a valve body according to an aspect. The pump assembly 1006 may include any of the features described with reference to the previous figures. The pump assembly 1006 includes a pump bulb, a valve body, a deflation mode actuator, the outer protective casing 1020, and fluid ports such as a first cylinder fluid port, a second cylinder fluid port, and a reservoir port. The outer protective casing 1020 includes a first end portion that defines a first opening, and a second end portion that defines a second opening. The pump bulb extends from the first opening, and the fluid ports extend from the second opening. The outer protective casing 1020 also defines a third opening. The deflation mode actuator extends through the third opening.

In the illustrated embodiment, the casing or the outer protective casing 1020 includes concave portions 1022 and 1024. The concave portions 1022 and 1024 may help the user detect the orientation and various features of the valve assembly 1006. For example, in some embodiments, the concave portions 1022 and 1024 may help the user detect the orientation and various features of the valve assembly 1006 after the assembly has been placed in the body of the user and bodily tissue has encapsulated the assembly. The outer protective casing 1020 also includes a ridge or a raised portion 1026 located on the side opposite the deflation button. The ridge or raised portion 1026 may also assist in feature detection by the user.

Figure 12:
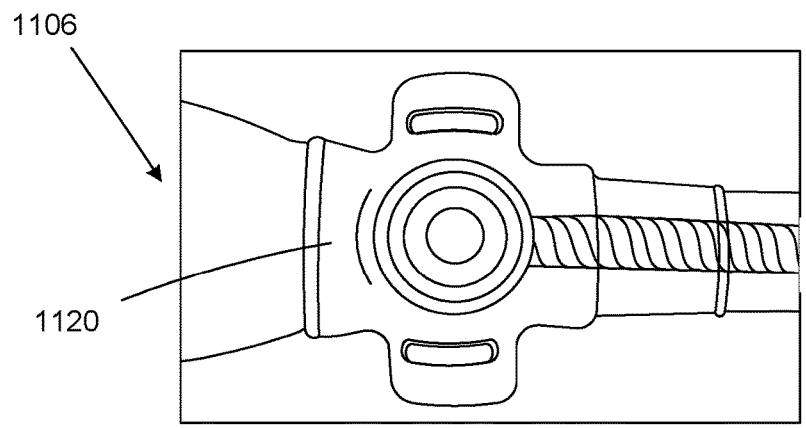
Figure 13:
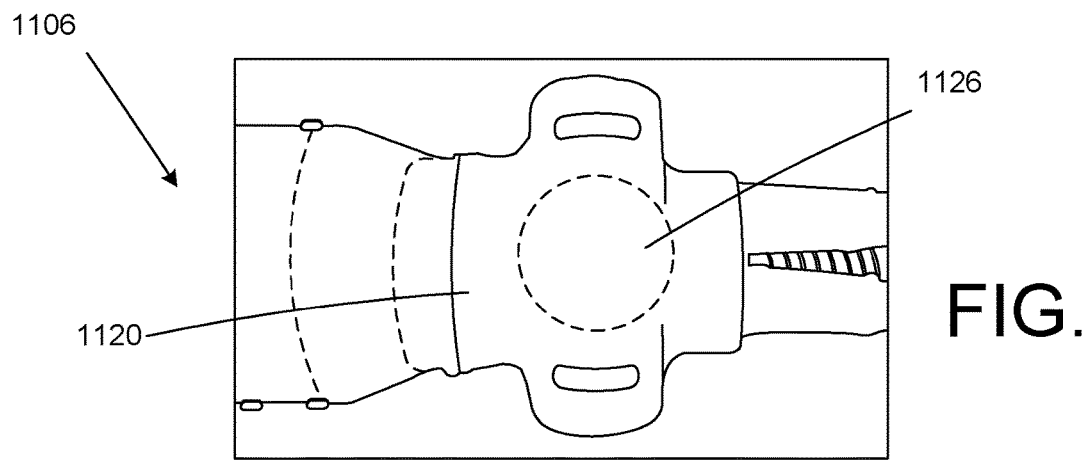
Figure 14:
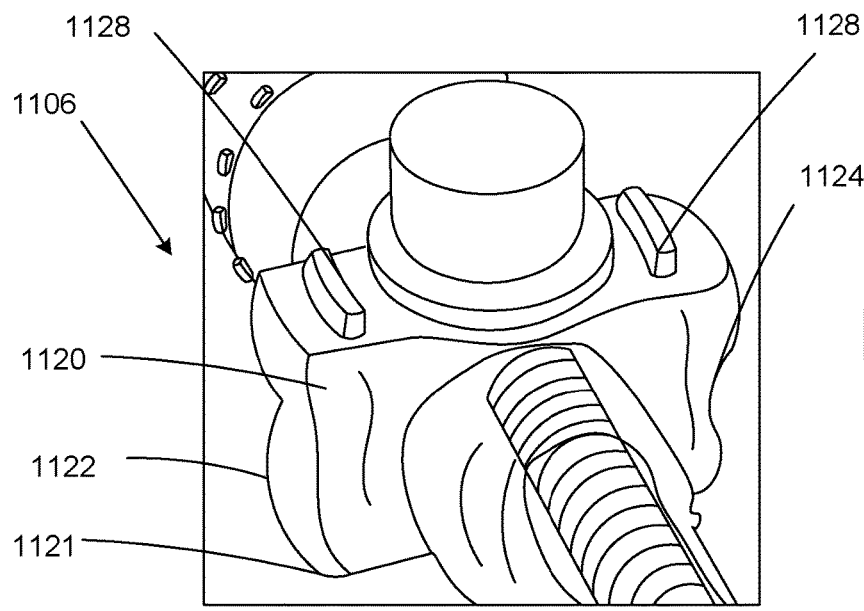

FIG. 12 is a top view of a pump assembly 1106. FIG. 13 is a bottom view of the pump assembly 1106. FIG. 14 is a perspective view of the pump assembly 1106. The pump assembly 1106 has an outer protective casing 1120 disposed over a valve body according to an aspect. The pump assembly 1106 may include any of the features described with reference to the previous figures. The pump assembly 1106 includes a pump bulb, a valve body, a deflation mode actuator, the outer protective casing 1120, and fluid ports such as a first cylinder fluid port, a second cylinder fluid port, and a reservoir port. The outer protective casing 1120 includes a first end portion that defines a first opening, and a second end portion that defines a second opening. The pump bulb extends from the first opening, and the fluid ports extend from the second opening. The outer protective casing 1120 also defines a third opening. The deflation mode actuator extends through the third opening.

In the illustrated embodiment, the casing or the outer protective casing 1120 includes concave portions 1122 and 1124 with curved or smooth edges 1121. The concave portions 1122 and 1124 may help the user detect the orientation and various features of the valve assembly 1106. For example, in some embodiments, the concave portions 1122 and 1124 may help the user detect the orientation and various features of the valve assembly 1106 after the assembly has been placed in the body of the user and bodily tissue has encapsulated the assembly. The outer protective casing 1120 also includes a ridge or a raised portion 1126 located on the side opposite the deflation button. The ridge or raised portion 1126 may also assist in feature detection by the user. In the illustrated embodiment, the outer protective casing 1120 also includes extension portions or grip features 1128.

Figure 15:
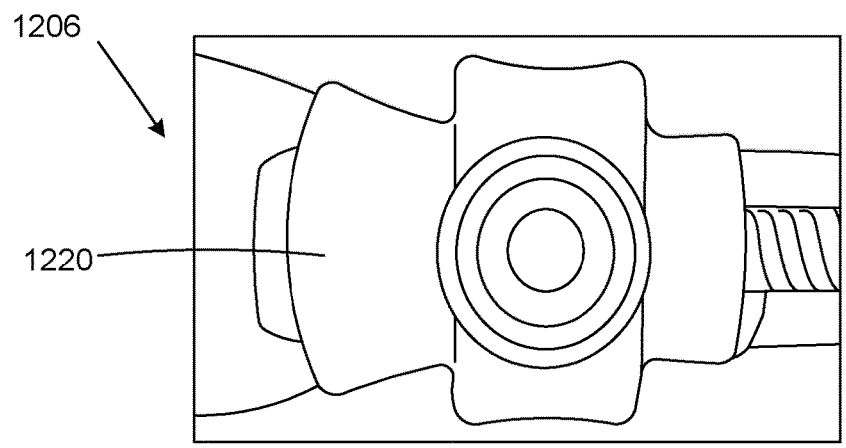
Figure 16:
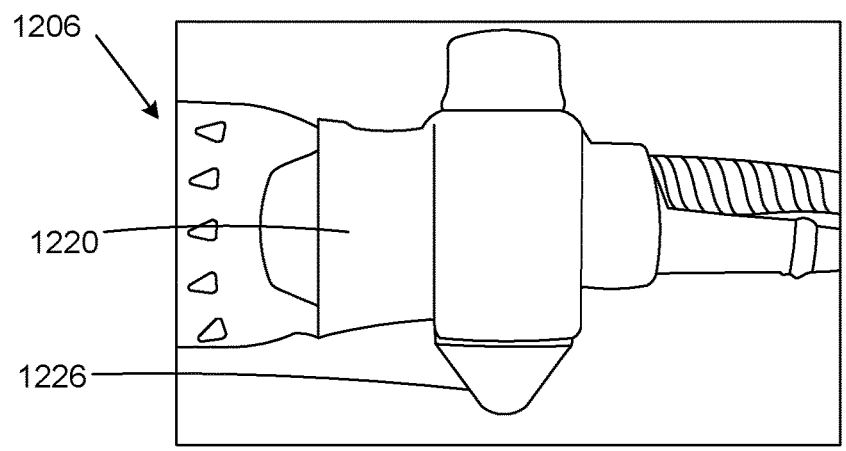
Figure 17:
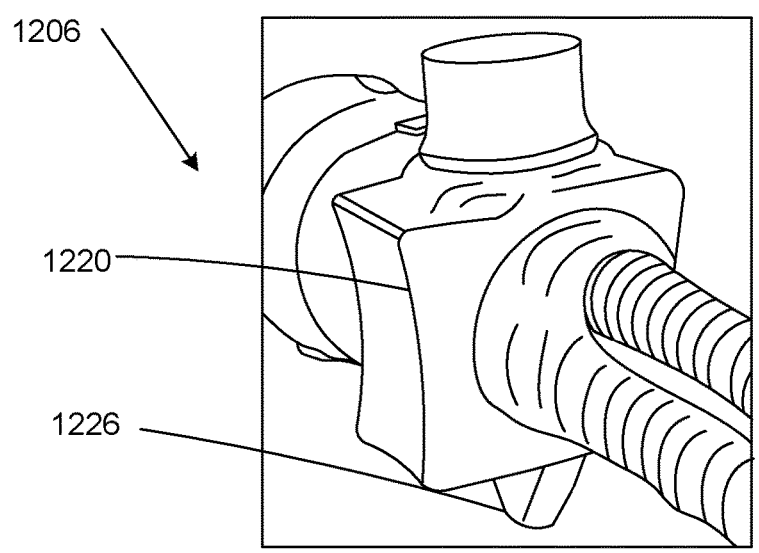

FIG. 15 is a top view of a pump assembly 1206. FIG. 16 is a bottom view of the pump assembly 1206. FIG. 17 is a perspective view of the pump assembly 1206. The pump assembly 1206 has an outer protective casing 1220 disposed over a valve body according to an aspect. The pump assembly 1206 may include any of the features described with reference to the previous figures. The pump assembly 1206 includes a pump bulb, a valve body, a deflation mode actuator, the outer protective casing 1220, and fluid ports such as a first cylinder fluid port, a second cylinder fluid port, and a reservoir port. The outer protective casing 1220 includes a first end portion that defines a first opening, and a second end portion that defines a second opening. The pump bulb extends from the first opening, and the fluid ports extend from the second opening. The outer protective casing 1220 also defines a third opening. The deflation mode actuator extends through the third opening.

In the illustrated embodiment, the casing or the outer protective casing 1220 includes a pointed member or dome member 1226 located on the side opposite the deflation button. The pointed member or dome member 1226 may assist in feature detection by the user.

FIGS. 18-44 illustrate various pump assemblies. The pump assemblies may include any of the features described with reference to the previous figures. The pump assemblies include a pump bulb, a valve body, a deflation mode actuator, the outer protective casing, and fluid ports such as a first cylinder fluid port, a second cylinder fluid port, and a reservoir port. The outer protective casing includes a first end portion that defines a first opening, and a second end portion that defines a second opening. The pump bulb extends from the first opening, and the fluid ports extend from the second opening. The outer protective casing also defines a third opening. The deflation mode actuator extends through the third opening.

Figure 18:
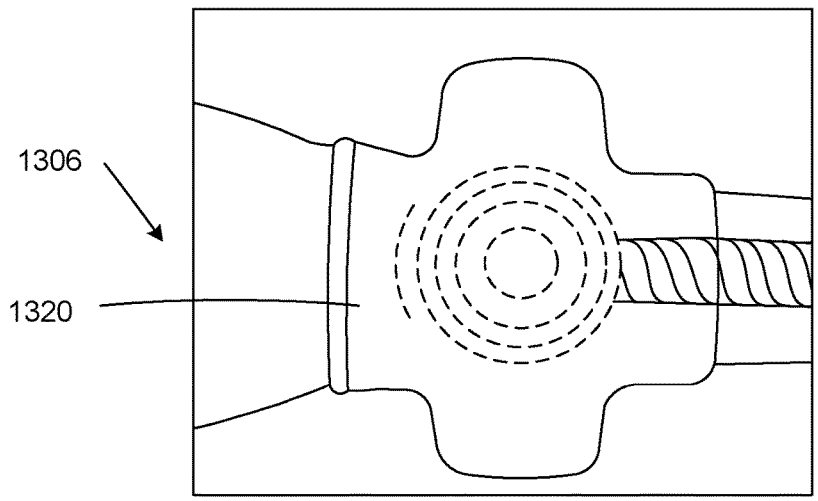
Figure 19:
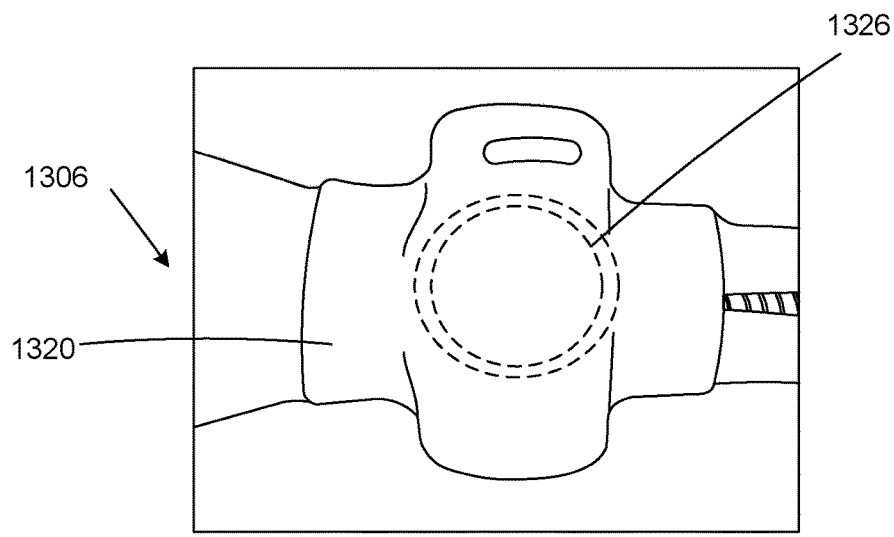
Figure 20:
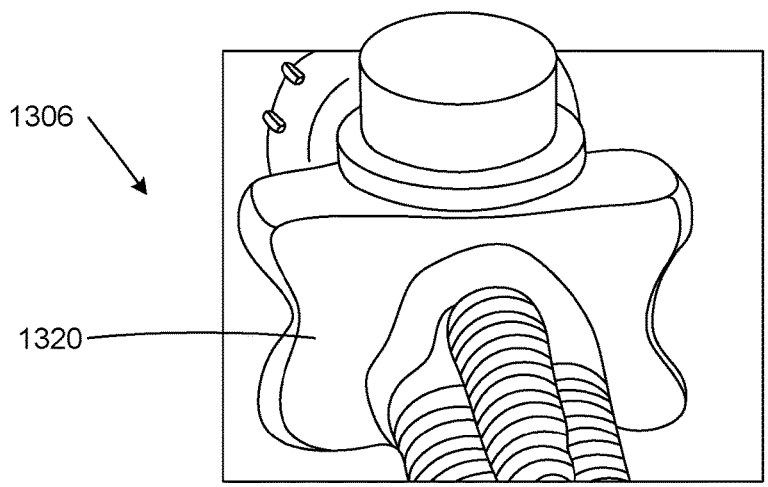

FIG. 18 is a top view of a pump assembly 1306. FIG. 19 is a bottom view of the pump assembly 1306. FIG. 20 is a perspective view of the pump assembly 1306. In the illustrated embodiment, the casing or the outer protective casing 1320 includes a concave portion 1326 located on the side opposite the deflation button. The concave portion 1326 may assist in feature detection by the user.

Figure 21:
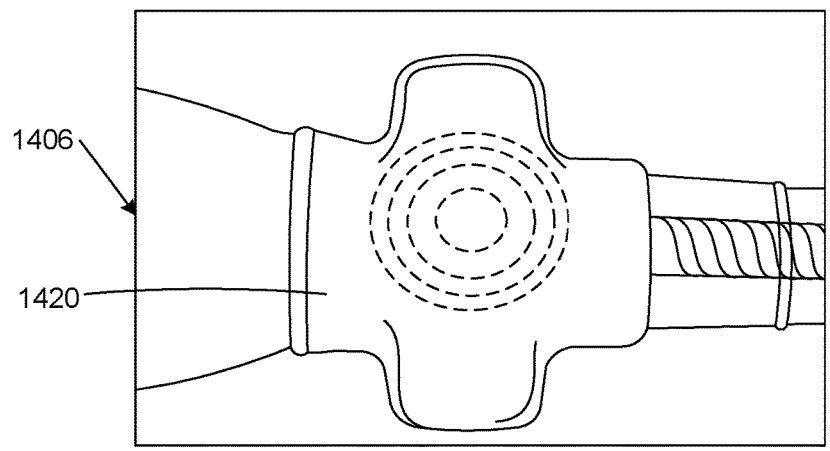
Figure 22:
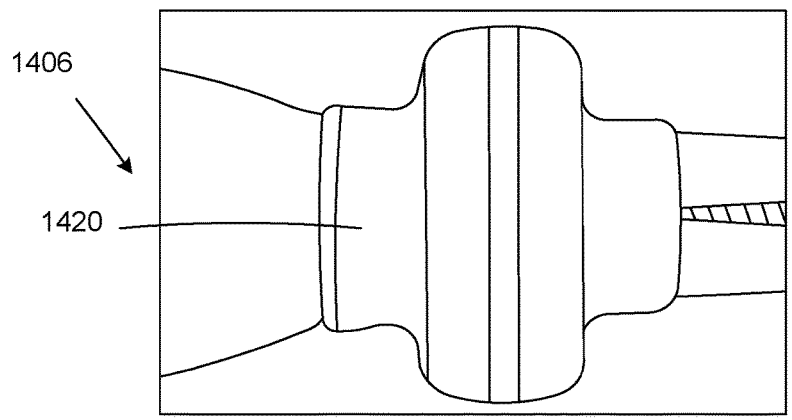
Figure 23:
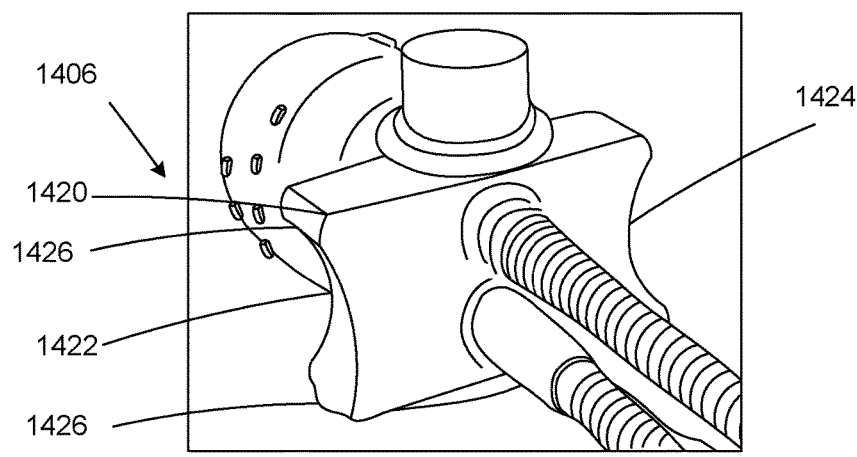

FIG. 21 is a top view of a pump assembly 1406. FIG. 22 is a bottom view of the pump assembly 1406. FIG. 23 is a perspective view of the pump assembly 1406. In the illustrated embodiment, the casing or the outer protective casing 1420 includes concave portions 1422 and 1424. The casing or outer protective casing 1420 also includes rounded or smooth corners 1426.

Figure 24:
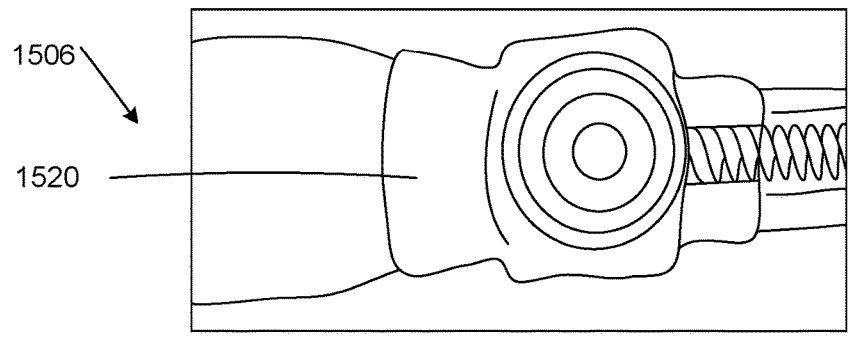
Figure 25:
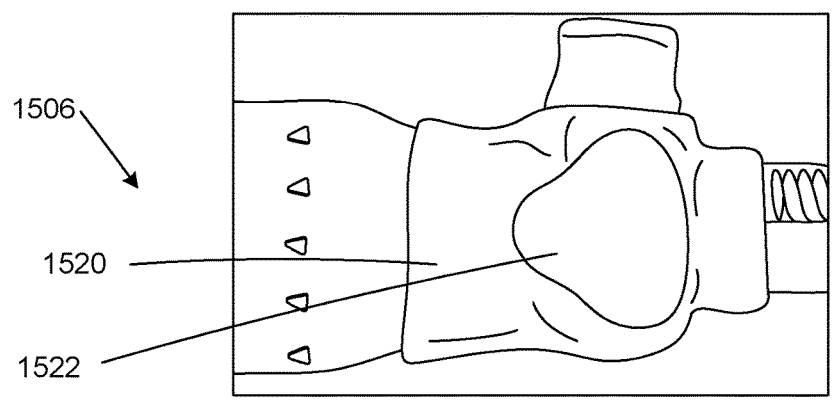
Figure 26:
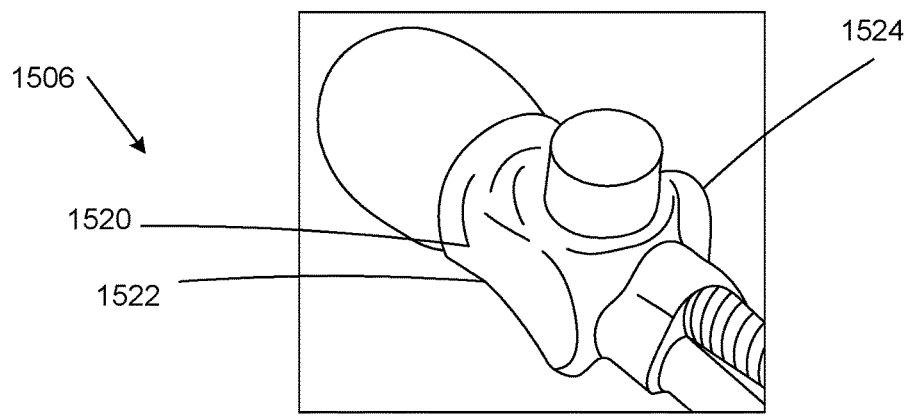

FIG. 24 is a top view of a pump assembly 1506. FIG. 25 is a bottom view of the pump assembly 1506. FIG. 26 is a perspective view of the pump assembly 1506. In the illustrated embodiment, the casing or the outer protective casing 1520 includes concave triangle shaped portions 1522 and 1524. The concave triangle portions 1522 and 1524 may assist in feature detection by the user.

Figure 27:
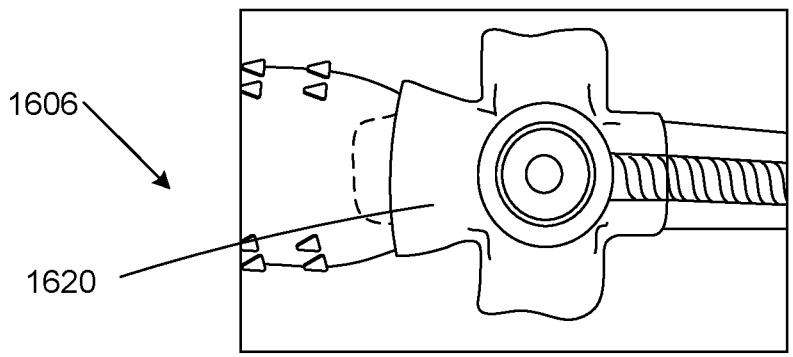
Figure 28:
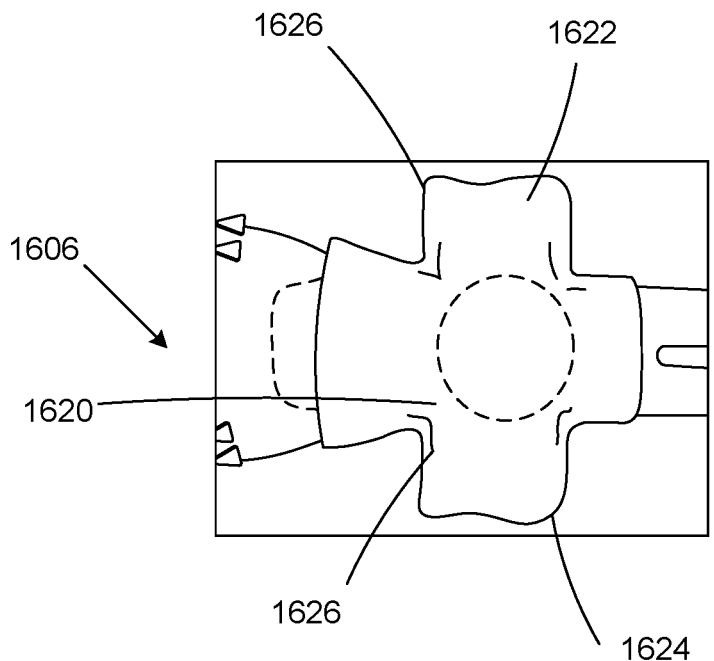
Figure 29:
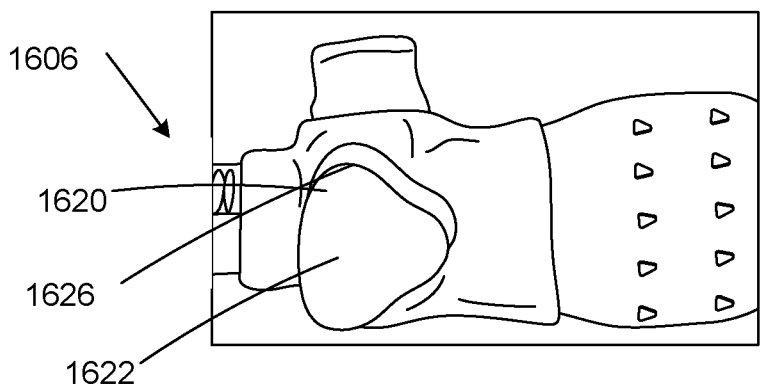

FIG. 27 is a top view of a pump assembly 1606. FIG. 28 is a bottom view of the pump assembly 1606. FIG. 29 is a side view of the pump assembly 1606. In the illustrated embodiment, the casing or outer protective casing 1620 includes extended or protruding side portions 1626. The casing or the outer protective casing 1620 also includes concave triangle shaped portions 1622 and 1624. The concave triangle portions 1622 and 1624 may assist in feature detection by the user.

Figure 30:
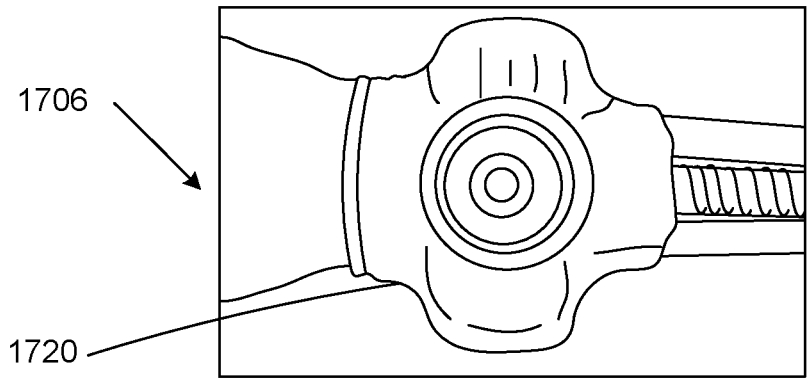
Figure 31:
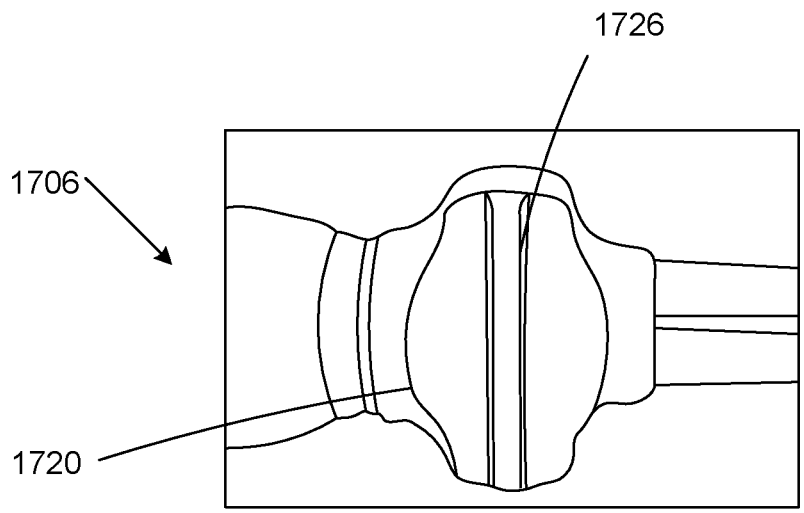
Figure 32:
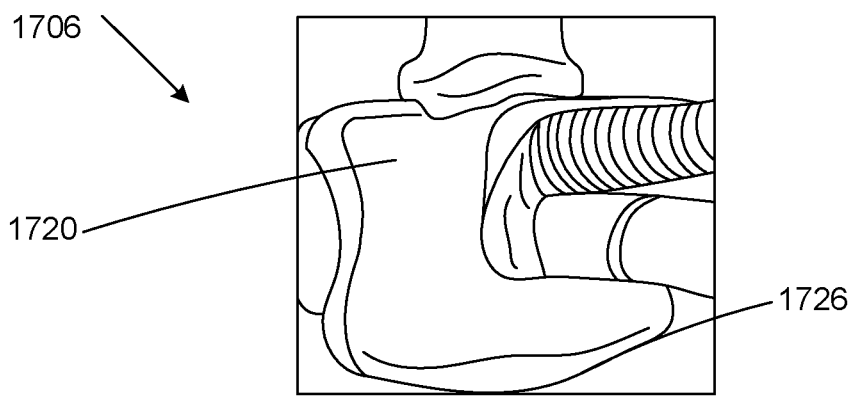

FIG. 30 is a top view of a pump assembly 1706. FIG. 31 is a bottom view of the pump assembly 1706. FIG. 32 is a perspective view of the pump assembly 1706. In the illustrated embodiment, the casing or outer protective casing 1720 includes protrusion or ridge 1726 that extends along the surface opposite the deflation button. In the illustrated embodiment, the protrusion or ridge 1726 extends along the entire length of the surface. The protrusion or ridge 1726 may assist in feature detection by the user.

Figure 33:
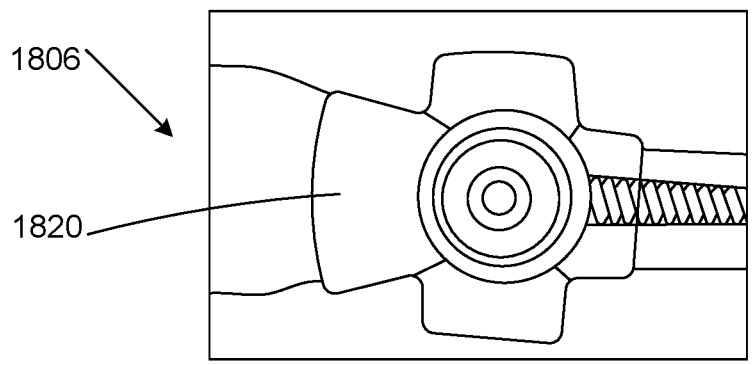
Figure 34:
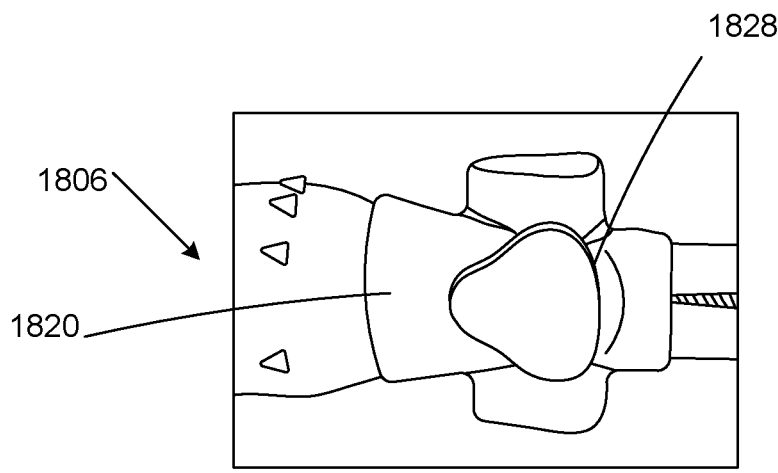
Figure 35:
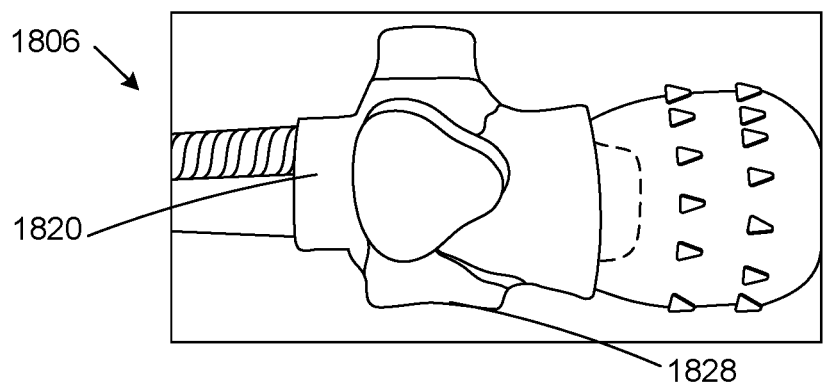

FIG. 33 is a top view of a pump assembly 1806. FIG. 34 is a bottom view of the pump assembly 1806. FIG. 35 is a side view of the pump assembly 1806. In the illustrated embodiment, the casing or outer protective casing 1820 includes an extension portion 1828 that extends from the surface opposite the deflation button. In the illustrated embodiment, the extension portion is triangular. In other embodiments, the extension portion has a different shape.

Figure 36:
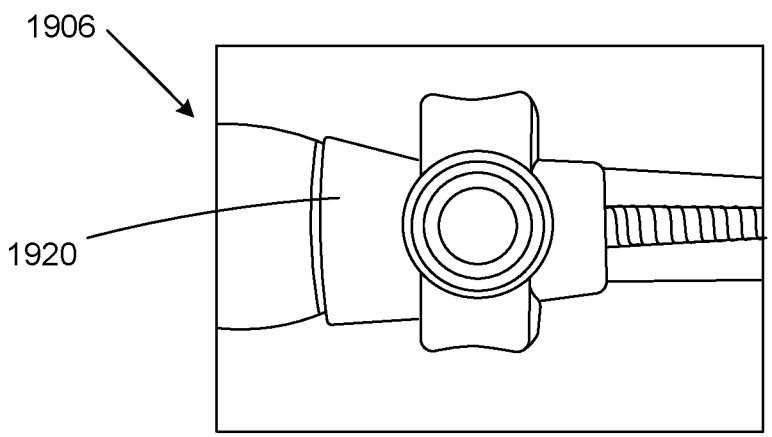
Figure 37:
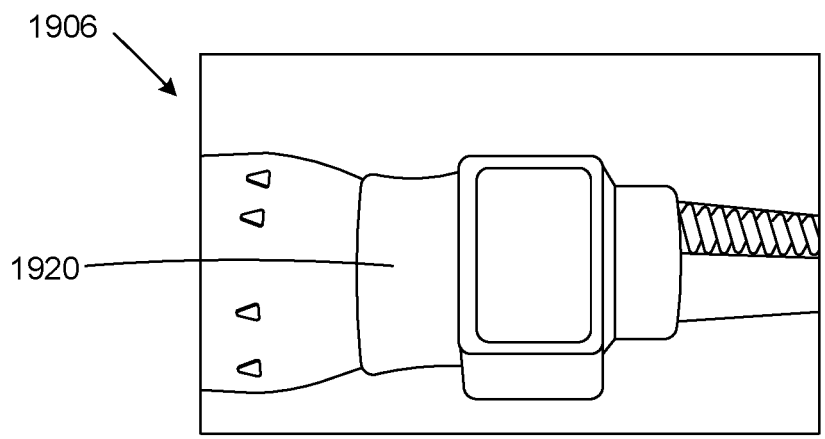
Figure 38:
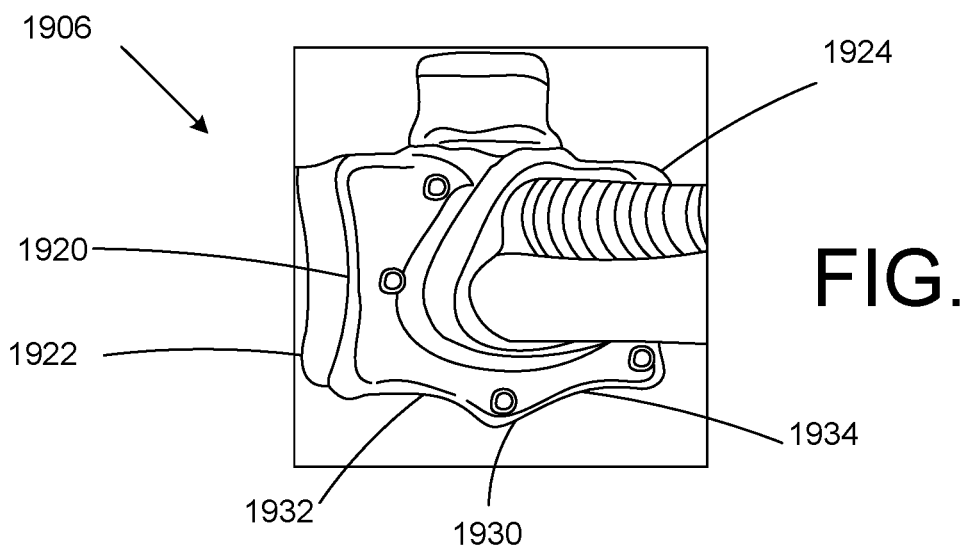

FIG. 36 is a top view of a pump assembly 1906. FIG. 37 is a bottom view of the pump assembly 1906. FIG. 38 is a perspective view of the pump assembly 1906. In the illustrated embodiment, the casing or outer protective casing 1920 includes curved side portions 1922 and 1924. The casing or outer protective casing 1920 also includes a bottom surface 1930 (the surface opposite the deflation button). The bottom surface 1930 includes a first finger portion 1932 (a concave or curved portion) and a second finger portion 1934 (a concave or curved portion). In some embodiments, the user may grasp the device such that a first finger is at the first finger portion 1932 and a second finger or a thumb is at the second finger portion 1934. In some embodiment, the orientation of the device facilitates the actuation of the deflate button.

Figure 39:
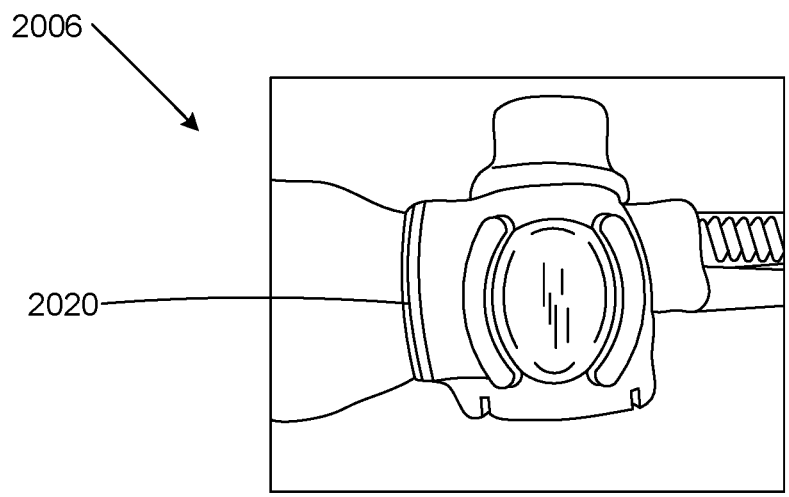
Figure 40:
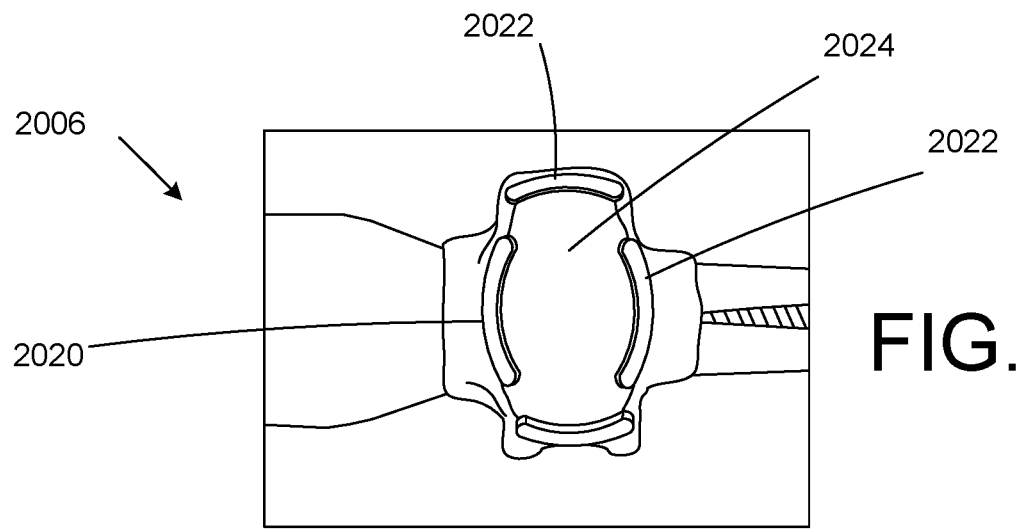
Figure 41:
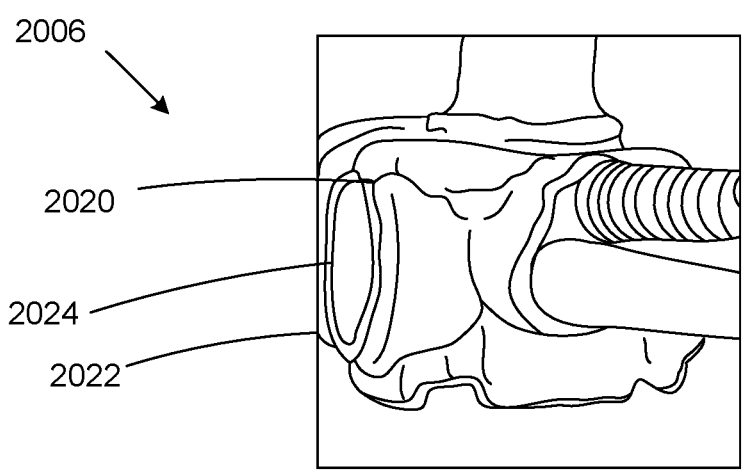

FIG. 39 is a top view of a pump assembly 2006. FIG. 40 is a bottom view of the pump assembly 2006. FIG. 41 is a perspective view of the pump assembly 2006. In the illustrated embodiment, the casing or outer protective casing 2020 includes sides that have edges 2022 and concave portions 2024.

Figure 42:
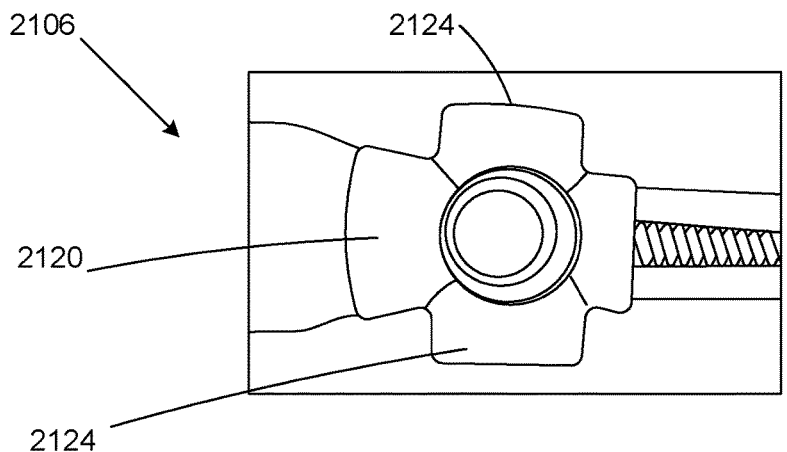
Figure 43:
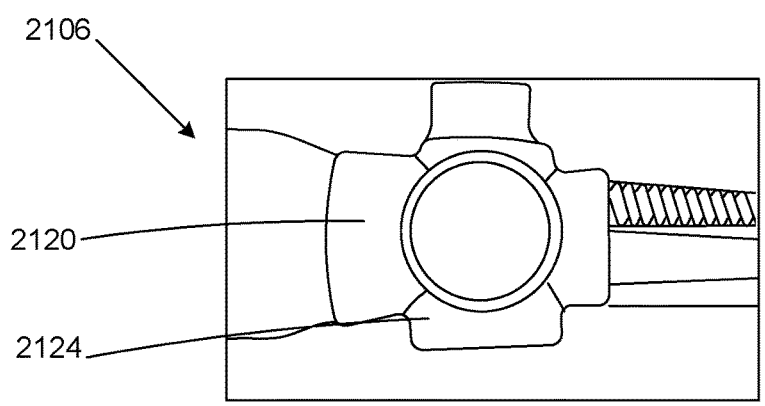
Figure 44:
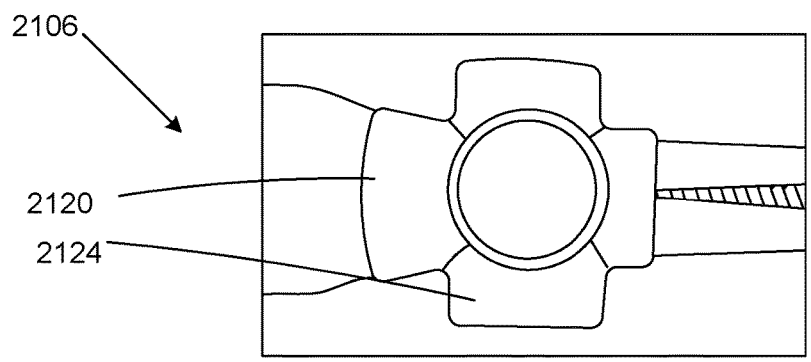
Figure 45:
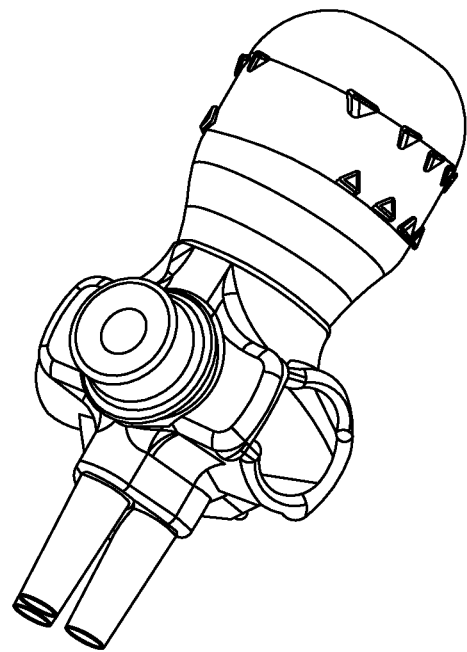
Figure 46:
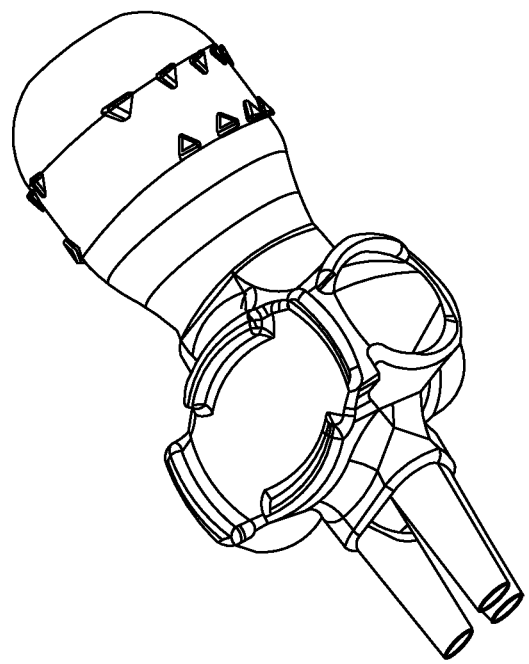
Figure 47:
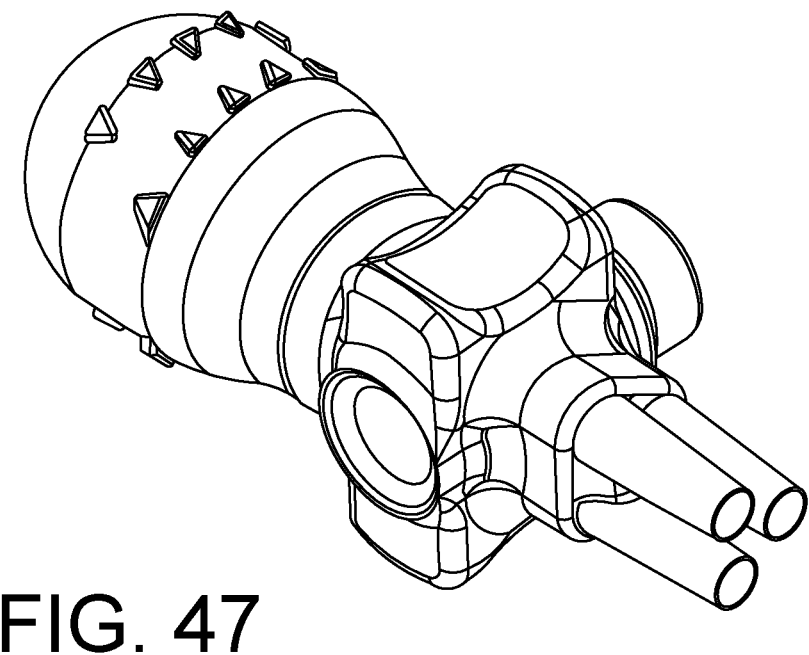
Figure 48:
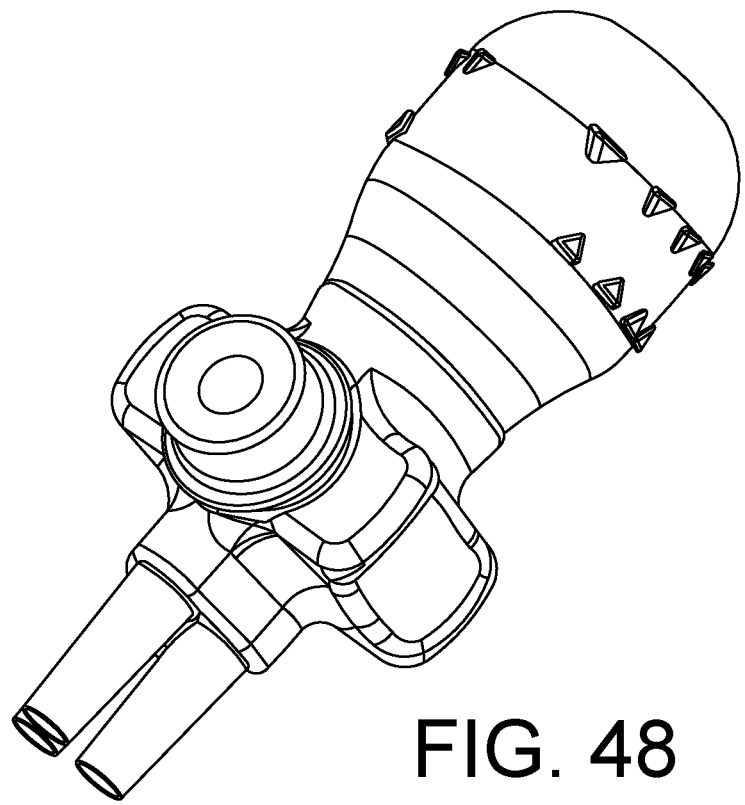
Figure 49:
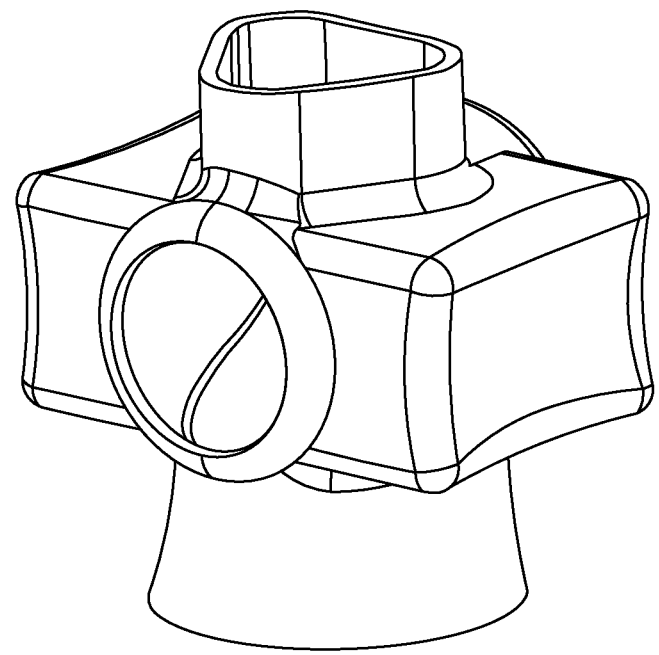
FIGS. 49-56 illustrate outer protective casings according to various aspects.
Figure 50:
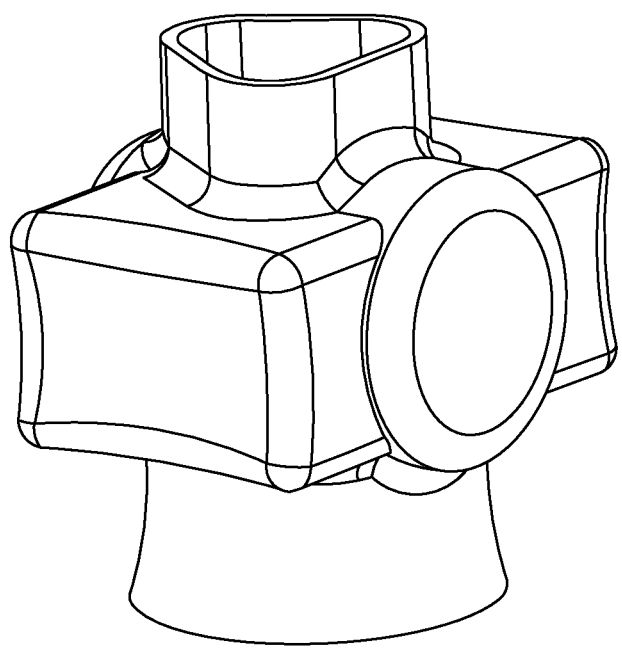
Figure 51:
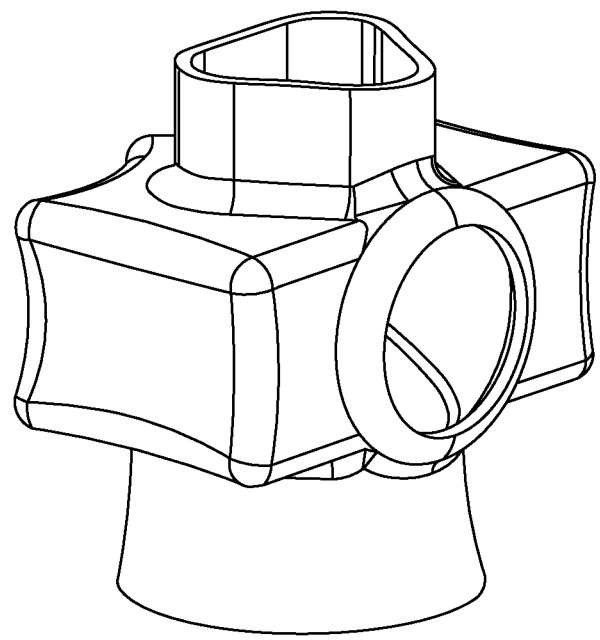
Figure 52:
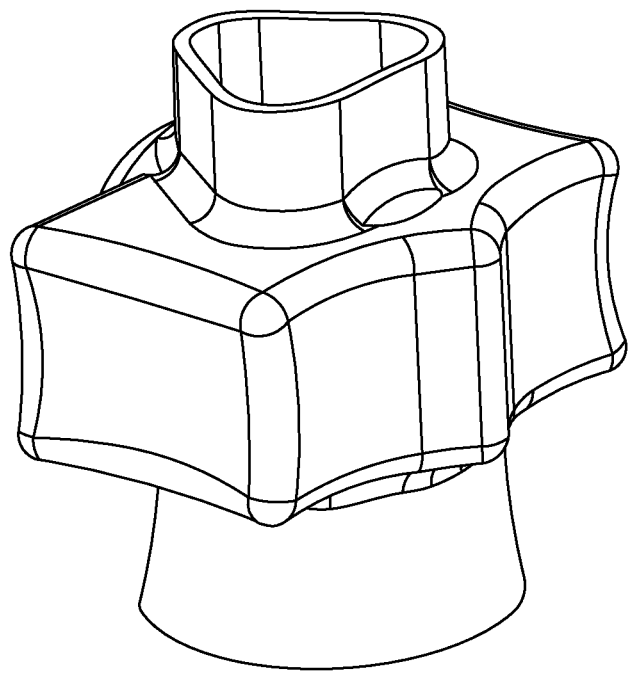
Figure 53:
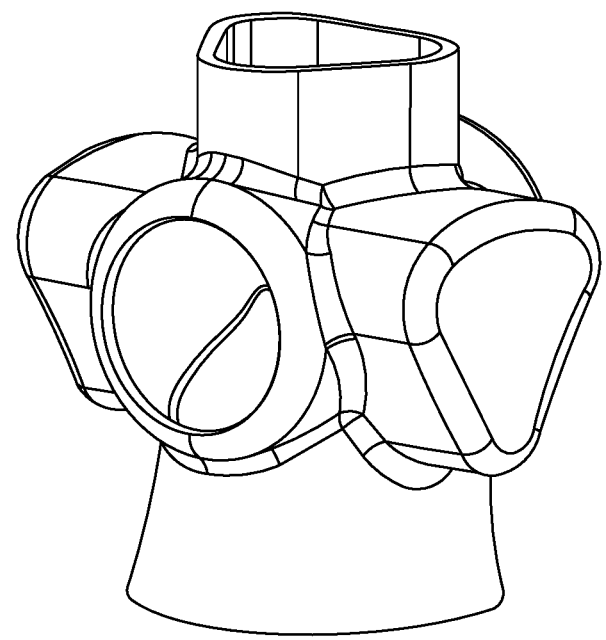
Figure 54:
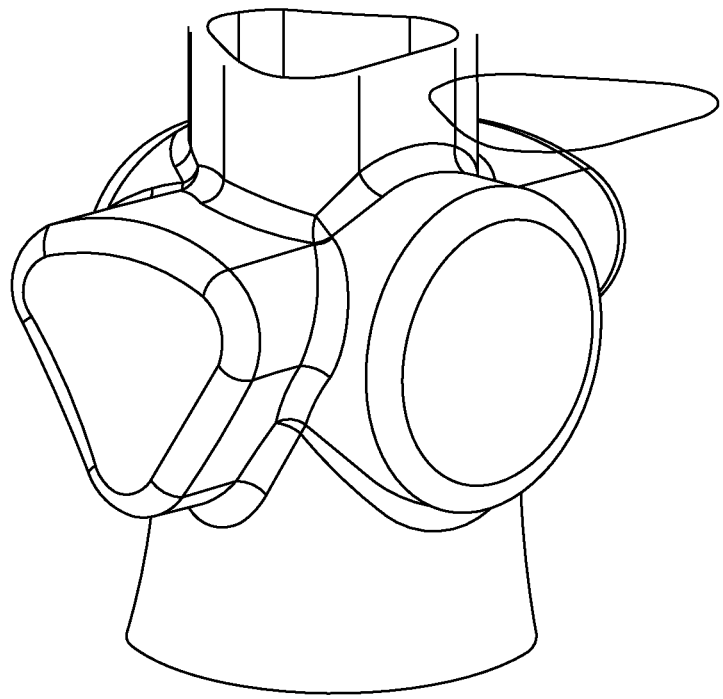
Figure 55:
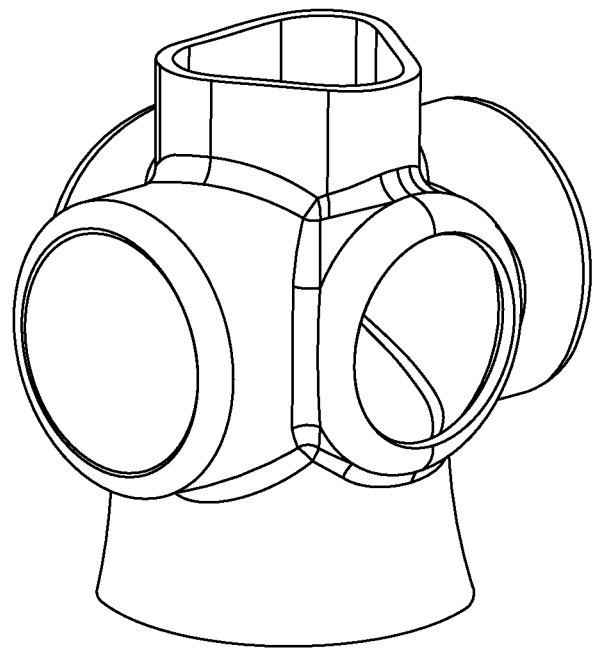
Figure 56:
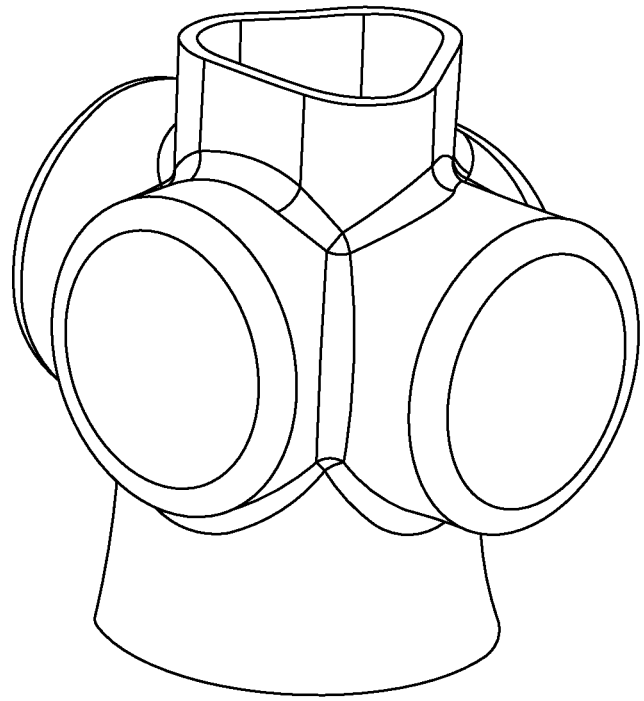

FIG. 42 is a top view of a pump assembly 2106. FIG. 43 is a side view of the pump assembly 2106. FIG. 44 is a bottom view of the pump assembly 2106. In the illustrated embodiment, the casing or outer protective casing 2120 includes sides that have circular concave portions 2024.

FIGS. 45-56 illustrate casings or outer protective casings according to various aspects.

Figure 59:
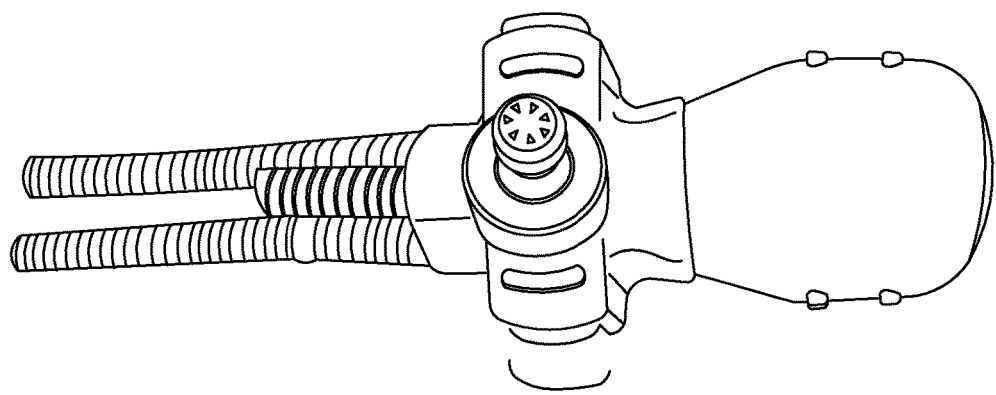
FIGS. 57-59 illustrate pump assemblies having outer protective casings according to various aspects.
Figure 58:
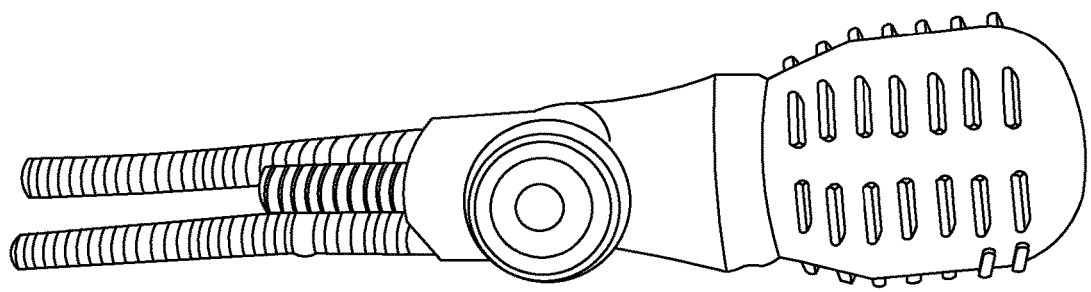
Figure 57:
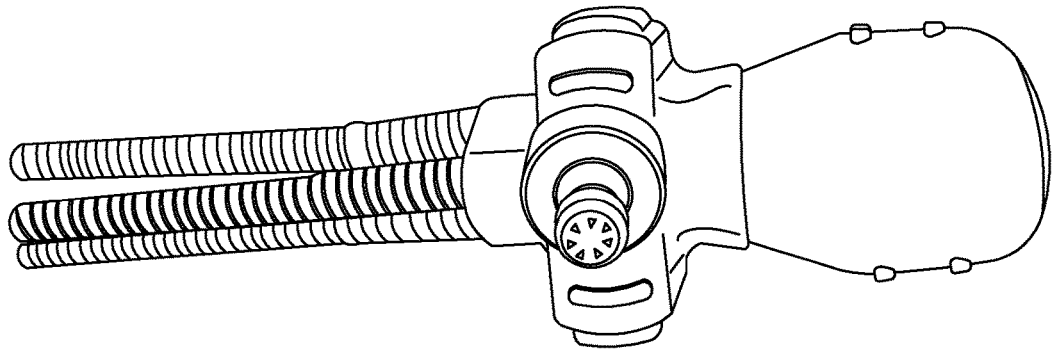

FIGS. 57-59 illustrate pump assemblies according to various aspects.

Figure 60:
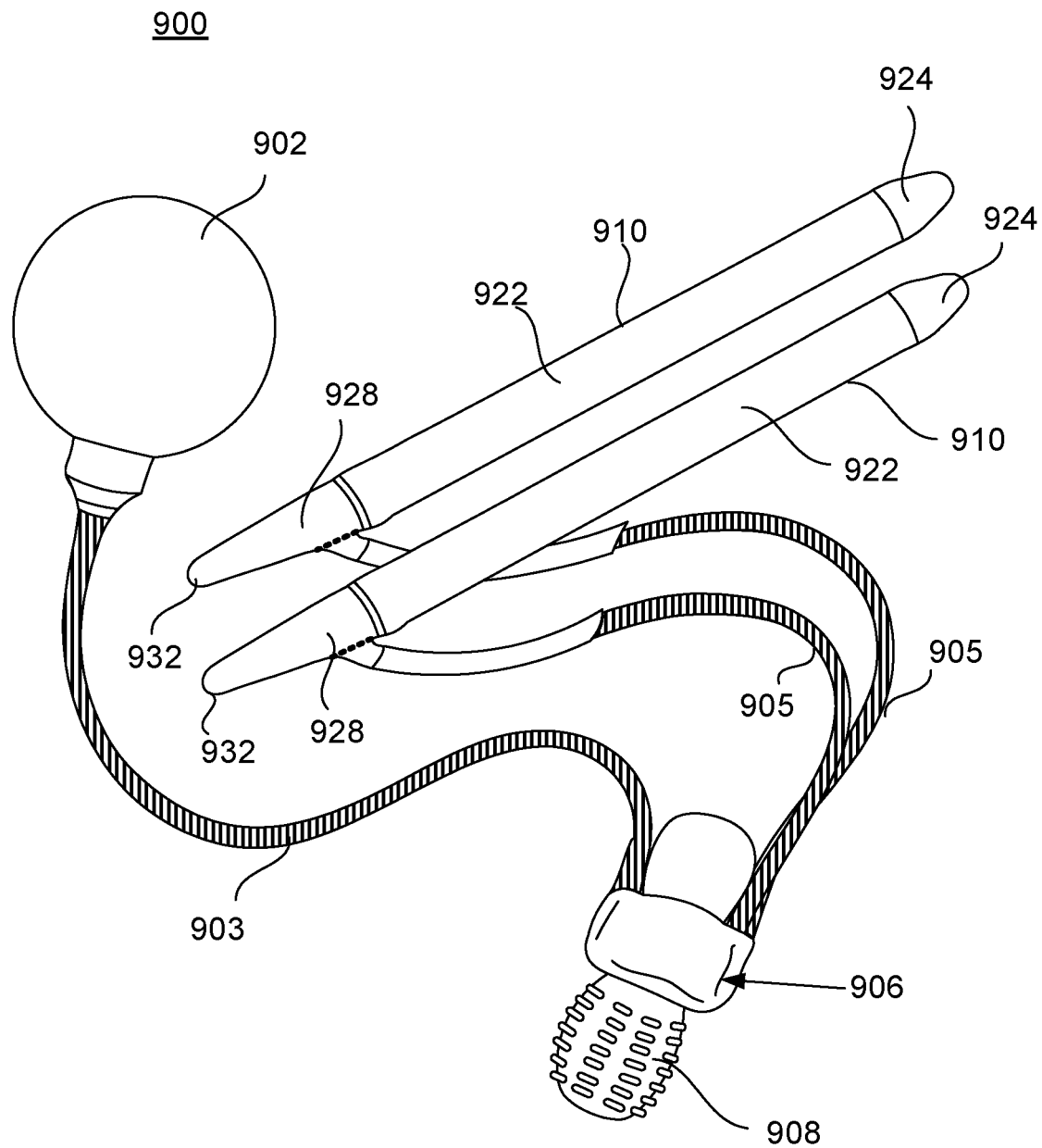
FIG. 60 illustrates an inflatable penile prosthesis according to an aspect.

FIG. 60 schematically illustrates an inflatable penile prosthesis 900 having a pump assembly 906 according to an aspect. The pump assembly 906 may be any of the previously-described pump assemblies (e.g., the pump assembly 906 may include any of the previously-described outer protection casings). The penile prosthesis 900 may include a pair of inflatable cylinders 910, and the inflatable cylinders 910 are configured to be implanted in a penis. For example, one of the inflatable cylinders 910 may be disposed on one side of the penis, and the other inflatable cylinder 910 may be disposed on the other side of the penis. Each inflatable cylinder 910 may include a first end portion 924, a cavity or inflation chamber 922, and a second end portion 928 having a rear tip 932.

The pump assembly 906 may be implanted into the patient's scrotum. A pair of conduit connectors 905 may attach the pump assembly 906 to the inflatable cylinders 910 such that the pump assembly 906 is in fluid communication with the inflatable cylinders 910. Also, the pump assembly 906 may be in fluid communication with a fluid reservoir 902 via a conduit connector 903. The fluid reservoir 902 may be implanted into the user's abdomen. The inflation chamber or portion 922 of the inflatable cylinder 910 may be disposed within the penis. The first end portion 924 of the inflatable cylinder 910 may be at least partially disposed within the crown portion of the penis. The second end portion 928 may be implanted into the patient's pubic region PR with the rear tip 932 proximate the pubic bone PB.

In order to implant the inflatable cylinders 910, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 910. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 928. The surgeon may measure the length of the corpora cavernosae from the incision and the dilated region of the pubic area to determine an appropriate size of the inflatable cylinders 910 to implant.

After the patient is prepared, the penile prosthesis 900 is implanted into the patient. The tip of the first end portion 924 of each inflatable cylinder 910 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 910 into the corpus cavernosum. This is done for each inflatable cylinder 910 of the pair. Once the inflation chamber 922 is in place, the surgeon may remove the suture from the tip. The surgeon then inserts the second end portion 928. The surgeon inserts the rear end of the inflatable cylinder 910 into the incision and forces the second end portion 928 toward the pubic bone PB until each inflatable cylinder 910 is in place.

A pump bulb 908 of the pump assembly 906 may be squeezed or depressed by the user in order to facilitate the transfer of fluid from the fluid reservoir 902 to the inflatable cylinders 910. For example, in the inflation mode, while the user is operating the pump bulb 908, the pump bulb 908 may receive the fluid from the fluid reservoir 902, and then output the fluid to the inflatable cylinders 910. When the user switches to the deflation mode, at least some of the fluid can automatically be transferred back to the fluid reservoir 902 (due to the difference in pressure from the inflatable cylinders 910 to the fluid reservoir 902). Then, the user may squeeze the inflatable cylinders 910 to facilitate the further transfer of fluid through the pump bulb 908 to the fluid reservoir 902.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis comprising:
a fluid reservoir configured to hold fluid;
an inflatable member; and
a pump assembly configured to transfer the fluid between the fluid reservoir and the inflatable member, the pump assembly including:
a valve body having one or more valves; and
an outer protective casing disposed over the valve body, the outer protective casing having a first side and a second side opposite the first side, the first side includes a central portion, a first protrusion extending from the central portion, and a second protrusion extending from the central portion, the first protrusion being disposed between the second side of the casing and the second protrusion.

2. The inflatable penile prosthesis of claim 1, wherein the outer protective casing includes a tactile feature configured to assist a user to locate a deflation mode actuator of the inflatable penile prosthesis.

3. The inflatable penile prosthesis of claim 2, wherein the tactile feature includes a plurality of ridges.

4. The inflatable penile prosthesis of claim 2, wherein the tactile feature includes a depression.

5. The inflatable penile prosthesis of claim 2, wherein the outer protective casing includes an opening, the deflation mode actuator extending through the opening of the outer protective casing.

6. The inflatable penile prosthesis of claim 1, wherein the pump assembly includes a pump bulb, a plurality of fluid ports, and a deflation mode actuator, the outer protective casing including a first end portion defining a first opening, and a second end portion defining a second opening, the outer protective casing defining a third opening, the pump bulb extending through the first opening, the plurality of fluid ports extending through the second opening, the deflation mode actuator extending through the third opening.

7. The inflatable penile prosthesis of claim 6, wherein the outer protective casing includes a protruded side portion having a three-dimensional shape, the protruded side portion having a surface that defines at least one ridge.

8. The inflatable penile prosthesis of claim 1, wherein the outer protective casing includes a polymer material.

9. The inflatable penile prosthesis of claim 1, wherein the outer protective casing includes a silicone material.

10. An inflatable penile prosthesis comprising:
a fluid reservoir configured to hold fluid;
an inflatable member; and a pump assembly configured to transfer the fluid between the fluid reservoir and the inflatable member, the pump assembly including:
a deflation mode actuator;
a valve body having one or more valves; and
an outer protective casing disposed over the valve body, wherein the pump assembly includes a pump bulb, a plurality of fluid ports, and a deflation mode actuator, the outer protective casing including a first end portion defining a first opening, and a second end portion defining a second opening, the outer protective casing defining a third opening, the pump bulb extending through the first opening, the plurality of fluid ports extending through the second opening, the deflation mode actuator extending through the third opening, wherein the outer protective casing includes a protruded side portion having a three-dimensional shape, the protruded side portion having a surface that defines at least one ridge.

11. The inflatable penile prosthesis of claim 10, wherein the tactile feature includes a plurality of ridges.

12. The inflatable penile prosthesis of claim 10, wherein the tactile feature includes a depression.

13. The inflatable penile prosthesis of claim 10, wherein the pump assembly includes a pump bulb, and a plurality of fluid ports, the outer protective casing including a first end portion defining a first opening, and a second end portion defining a second opening, the outer protective casing defining a third opening, the pump bulb extending through the first opening, the plurality of fluid ports extending through the second opening, the deflation mode actuator extending through the third opening.

14. The inflatable penile prosthesis of claim 10, wherein the outer protective casing includes:
a first protruded side portion; and
a second protruded side portion, at least one of the first protruded side portion and the second protruded side portion defining at least one ridge.

15. The inflatable penile prosthesis of claim 10, wherein the outer protective casing includes a central portion, and a plurality of projections extending from the central portion, the plurality of projections defining at least one groove.

16. The inflatable penile prosthesis of claim 10, wherein the outer protective casing includes a material that is different than the valve body.

17. A pump assembly for an inflatable penile prosthesis comprising:
a valve body having one or more valves;
a deflation mode actuator movably coupled to the valve body;
a pump bulb coupled to the valve body;
one or more fluid ports coupled to the valve body; and
an outer protective casing disposed over the valve body, the outer protective casing having a first side and a second side opposite the first side, the first side includes a central portion, a first protrusion extending from the central portion, and a second protrusion extending from the central portion, the first protrusion being disposed between the second side of the casing and the second protrusion.

18. The pump assembly of claim 17, wherein the outer protective casing includes a first end portion defining a first opening, a second end portion defining a second opening, and a side portion defining a third opening, the pump bulb extending through the first opening, the one or more fluid ports extending through the third opening, the deflation mode actuator extending through the third opening.

19. The pump assembly of claim 17, wherein the tactile feature includes one or more ridges.

20. The pump assembly of claim 17, wherein the tactile feature includes one or more depressions.

* * * * *